(12) United States Patent
Messersmith et al.

(10) Patent No.: US 7,618,937 B2
(45) Date of Patent: Nov. 17, 2009

(54) PEPTIDOMIMETIC POLYMERS FOR ANTIFOULING SURFACES

(75) Inventors: Phillip B. Messersmith, Claredon Hills, IL (US); Annelise Barron, Chicago, IL (US); Andrea Statz, Evanston, IL (US); Robert Meagher, Mountain House, CA (US)

(73) Assignee: Northwestern University, Evanston, IL (US)

( * ) Notice: Subject to any disclaimer, the term of this patent is extended or adjusted under 35 U.S.C. 154(b) by 49 days.

(21) Appl. No.: 11/280,107

(22) Filed: Nov. 16, 2005

(65) Prior Publication Data

US 2006/0241281 A1  Oct. 26, 2006

Related U.S. Application Data

(63) Continuation-in-part of application No. 11/068,298, filed on Feb. 27, 2005, and a continuation-in-part of application No. 11/179,218, filed on Jul. 11, 2005.

(60) Provisional application No. 60/306,750, filed on Jul. 20, 2001, provisional application No. 60/373,919, filed on Apr. 29, 2002, provisional application No. 60/549,259, filed on Mar. 2, 2004, provisional application No. 60/548,314, filed on Feb. 27, 2004, provisional application No. 60/628,359, filed on Nov. 16, 2004, provisional application No. 60/586,742, filed on Jul. 9, 2004.

(51) Int. Cl.
| | |
|---|---|
| A61K 38/00 | (2006.01) |
| A01N 37/18 | (2006.01) |
| A61M 36/14 | (2006.01) |
| A61K 51/00 | (2006.01) |
| D21H 19/50 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |

(52) U.S. Cl. .................. 514/2; 530/300; 524/17; 424/1.69

(58) Field of Classification Search .................. 514/2; 530/300; 524/17; 424/1.69
See application file for complete search history.

(56) References Cited

U.S. PATENT DOCUMENTS

| | | |
|---|---|---|
| 4,339,561 A | 7/1982 | Jacquet et al. |
| 4,496,397 A | 1/1985 | Waite |
| 4,585,585 A | 4/1986 | Waite |
| 4,615,697 A | 10/1986 | Robinson |
| 4,687,740 A | 8/1987 | Waite |
| 4,795,436 A | 1/1989 | Robinson |
| 4,808,702 A | 2/1989 | Waite |
| 4,908,404 A | 3/1990 | Benedict et al. |
| 4,978,336 A | 12/1990 | Capozzi et al. |
| 4,983,392 A | 1/1991 | Robinson |
| 5,015,677 A | 5/1991 | Benedict et al. |
| 5,024,933 A | 6/1991 | Yang et al. |
| 5,030,230 A | 7/1991 | White |
| 5,049,504 A | 9/1991 | Maugh et al. |
| 5,098,999 A | 3/1992 | Yamamoto et al. |
| 5,108,923 A | 4/1992 | Benedict et al. |
| 5,116,315 A | 5/1992 | Capozzi et al. |
| 5,156,956 A | 10/1992 | Motoki et al. |
| 5,192,316 A | 3/1993 | Ting |
| 5,197,973 A | 3/1993 | Pang et al. |
| 5,202,236 A | 4/1993 | Maugh et al. |
| 5,202,256 A | 4/1993 | Maugh et al. |
| 5,225,196 A | 7/1993 | Robinson |
| 5,242,808 A | 9/1993 | Maugh et al. |
| 5,260,194 A | 11/1993 | Olson |
| 5,374,431 A | 12/1994 | Pang et al. |
| 5,410,023 A | 4/1995 | Burzio |
| 5,428,014 A | 6/1995 | Labroo et al. |
| 5,487,739 A | 1/1996 | Aebischer et al. |
| 5,490,980 A | 2/1996 | Richardson et al. |
| 5,520,727 A | 5/1996 | Vreeland et al. |
| 5,525,336 A | 6/1996 | Green et al. |
| 5,549,904 A | 8/1996 | Juergensen et al. |
| 5,563,047 A | 10/1996 | Petersen |
| 5,574,134 A | 11/1996 | Waite |
| 5,580,697 A | 12/1996 | Keana et al. |
| 5,582,955 A | 12/1996 | Keana et al. |
| 5,605,938 A | 2/1997 | Roufa et al. |
| 5,618,551 A | 4/1997 | Tardy et al. |

(Continued)

FOREIGN PATENT DOCUMENTS

DE   196 43 007 A 1   4/1998

(Continued)

OTHER PUBLICATIONS

Statz et al. New peptidomimetic polymers for antifouling surfaces. JACS (May 16, 2005), 127(22), 7972-7973.*

(Continued)

*Primary Examiner*—Cecilia Tsang
*Assistant Examiner*—Maury Audet
(74) *Attorney, Agent, or Firm*—Quarles & Brady, LLP

(57) ABSTRACT

Peptidomimetic polymers comprising one or more DOPA moieties and related coatings and composites.

10 Claims, 5 Drawing Sheets

U.S. PATENT DOCUMENTS

| | | | |
|---|---|---|---|
| 5,628,793 A | 5/1997 | Zirm | |
| 5,705,177 A | 1/1998 | Roufa et al. | |
| 5,705,178 A | 1/1998 | Roufa et al. | |
| 5,736,132 A | 4/1998 | Juergensen et al. | |
| 5,776,747 A | 7/1998 | Schinstine et al. | |
| 5,800,828 A | 9/1998 | Dionne et al. | |
| 5,817,470 A | 10/1998 | Burzio et al. | |
| 5,830,539 A | 11/1998 | Yan et al. | |
| 5,834,232 A | 11/1998 | Bishop et al. | |
| 5,858,747 A | 1/1999 | Schinstine et al. | |
| 5,935,849 A | 8/1999 | Schinstine et al. | |
| 5,939,385 A | 8/1999 | Labroo et al. | |
| 5,955,096 A | 9/1999 | Santos et al. | |
| 5,968,568 A | 10/1999 | Kuraishi et al. | |
| 5,985,312 A | 11/1999 | Jacob et al. | |
| 5,994,325 A | 11/1999 | Roufa et al. | |
| 6,010,871 A | 1/2000 | Takahara et al. | |
| 6,020,326 A | 2/2000 | Roufa et al. | |
| 6,022,597 A | 2/2000 | Yan et al. | |
| 6,083,930 A | 7/2000 | Roufa et al. | |
| 6,093,686 A | 7/2000 | Nakada et al. | |
| 6,129,761 A | 10/2000 | Hubbell | |
| 6,150,461 A | 11/2000 | Takei et al. | |
| 6,156,348 A | 12/2000 | Santos et al. | |
| 6,162,903 A | 12/2000 | Trowern et al. | |
| 6,235,313 B1 | 5/2001 | Mathiowitz et al. | |
| 6,267,957 B1 | 7/2001 | Green et al. | |
| 6,284,267 B1 | 9/2001 | Aneja | |
| 6,294,187 B1 | 9/2001 | Boyce et al. | |
| 6,306,993 B1 | 10/2001 | Rothbard et al. | |
| 6,309,669 B1 | 10/2001 | Setterstrom et al. | |
| 6,322,996 B1 | 11/2001 | Sato et al. | |
| 6,325,951 B1 | 12/2001 | Soper et al. | |
| 6,331,422 B1 | 12/2001 | Hubbell et al. | |
| 6,335,430 B1 | 1/2002 | Qvist | |
| 6,365,187 B2 | 4/2002 | Mathiowitz et al. | |
| 6,368,586 B1 | 4/2002 | Jacob et al. | |
| 6,417,173 B1 | 7/2002 | Roufa et al. | |
| 6,486,213 B1 | 11/2002 | Chen et al. | |
| 6,491,903 B1 | 12/2002 | Forster et al. | |
| 6,497,729 B1 | 12/2002 | Moussy et al. | |
| 6,506,577 B1 | 1/2003 | Deming et al. | |
| 6,555,103 B2 | 4/2003 | Leukel et al. | |
| 6,565,960 B2 | 5/2003 | Koob et al. | |
| 6,566,074 B1 | 5/2003 | Goetinck | |
| 6,566,406 B1 | 5/2003 | Pathak et al. | |
| 6,635,274 B1 | 10/2003 | Masiz et al. | |
| 6,663,883 B1 | 12/2003 | Akiyama et al. | |
| 6,821,530 B2 | 11/2004 | Koob et al. | |
| 6,887,845 B2 | 5/2005 | Barron et al. | |
| 7,009,034 B2 | 3/2006 | Pathak et al. | |
| 7,208,171 B2 | 4/2007 | Messersmith et al. | |
| 7,300,991 B2 | 11/2007 | Nishimura et al. | |
| 2001/0043940 A1 | 11/2001 | Boyce et al. | |
| 2001/0049400 A1 | 12/2001 | Alli et al. | |
| 2002/0022013 A1 | 2/2002 | Leukel et al. | |
| 2002/0049290 A1 | 4/2002 | Vanderbilt | |
| 2002/0182633 A1 | 12/2002 | Chen et al. | |
| 2003/0009235 A1 | 1/2003 | Manrique et al. | |
| 2003/0012734 A1 | 1/2003 | Pathak et al. | |
| 2003/0039676 A1 | 2/2003 | Boyce et al. | |
| 2003/0065060 A1 | 4/2003 | Qvist et al. | |
| 2003/0069205 A1 | 4/2003 | Roufa et al. | |
| 2003/0087338 A1 | 5/2003 | Messersmith et al. | |
| 2003/0099682 A1 | 5/2003 | Moussy et al. | |
| 2003/0109587 A1 | 6/2003 | Mori | |
| 2003/0208888 A1 | 11/2003 | Fearing et al. | |
| 2004/0005421 A1 | 1/2004 | Gervasi et al. | |
| 2004/0028646 A1 | 2/2004 | Gross et al. | |
| 2005/0032929 A1 | 2/2005 | Greener | |
| 2005/0288398 A1 | 12/2005 | Messersmith et al. | |
| 2006/0009550 A1 | 1/2006 | Messersmith et al. | |

FOREIGN PATENT DOCUMENTS

| | | |
|---|---|---|
| WO | WO 88/03953 | 6/1988 |
| WO | WO 92/10567 | 6/1992 |
| WO | WO 94/28937 | 12/1994 |
| WO | WO 97/34016 | 9/1997 |
| WO | WO 98/07076 | 2/1998 |
| WO | WO 01/44401 A1 | 6/2001 |
| WO | WO 02/34764 A1 | 5/2002 |
| WO | WO 03/008376 A2 | 1/2003 |
| WO | WO 03/080137 A1 | 10/2003 |
| WO | WO 2004/042068 A2 | 5/2004 |

OTHER PUBLICATIONS

Dalsin et al., Bioinspired Antifouling Polymers. Materials Today 2005, 8, 9 (38-46).

Gristina, Biomaterial-Centered Infection—Microbial Adhesion Versus Tissue Integration. Science 1987, 237, (4822), 1588-1595.

Evans et al., Iron Chelator, Exopolysaccharide and Protease Production in *Staphylococcus-epidermidis*—a Comparative-Study of the Effects of Specific Growth-Rate in Biofilm and Planktonic Culture. Microbiology-Uk 1994, 140, 153-157.

Yu et al., Adhesion of Coagulase-Negative Staphylococci and Adsorption of Plasma-Proteins to Heparinized Polymer Surfaces. Biomaterials 1994,15, (10), 805-814.

Jose et al., Vancomycin covalently bonded to titanium beads kills *Staphylococcus aureus*. Chemistry & Biology 2005, 12, (9), 1041-1048.

Desai et al., Surface-Immobilized Polyethylene Oxide for Bacterial Repellence. Biomaterials 1992, 13, (7), 417-420.

Burdinski et al., Universal Ink for Microcontact Printing. Angwandte Chemie 2006, 45, 1-5.

Floriolli et al., Marine surfaces and the expression of specific byssal adhesive protein variants in Mytilus. Mar Biotechnol 2000, 2, 352-363.

Bain et al., Molecular-level Control over Surface Order in Self-Assembled Monolayer Films of Thiols on Gold. Science 1988, 240, (4848), 62-63.

Waite, Reverse engineering of bioadhesion in marine mussels. Bioartificial Organs ii: Technology, Medicine, and Materials 1999, 875, 301-309.

Pasche et al., Poly(l-lysine)-graft-poly(ethylene glycol) assembled monolayers on niobium oxide surfaces: A quantitative study of the influence of polymer interfacial architecture on resistance to protein adsorption by ToF-SIMS and in situ OWLS. Langmuir 2003,19, (22), 9216-9225.

Zhang et al., Reactive coupling of poly(ethylene glycol) on electroactive polyaniline films for reduction in protein adsorption and platelet adhesion. Biomaterials 2002, 23, (3), 787-795.

Holl et al., Solid-State NMR Analysis of Cross-Linking in Mussel Protein Glue. Archives of Biochemistry and Biophysics 1993, 302, (1),255-258.

International Search Report, PCT/US2008/050721.

Advincula, "Surface Initiated Polymerization from Nanoparticle Surfaces," *J. Dispersion Sci. Technol.*, vol. 24, Nos. 3 & 4 (2003), pp. 343-361.

Ahmed, et al., "Synthesis and Application of Fluorescein-Labeled Pluronic Block Copolymers to the Study of Polymer-Surface Interactions," *Langmuir*, vol. 17, No. 2 (2001), pp. 537-546.

Alexandridis, P.; Nivaggioli, T.; Hatton, T. A., "Temperature Effects on Structural Properties of Pluronic P104 and F108 PEO-PPO-PEO Block Copolymer Solutions," *Langmuir*, vol. 11, No. 5 (1995), pp. 1468-1476.

Alexandridis, P., "Poly(ethylene oxide)-Poly(propylene oxide) Block Copolymer Surfactants," *Curr. Opin. Colloid Interface Sci.*, vol. 2, No. 5 (1997), pp. 478-489.

Alivisatos, P., "The use of nanocrystals in biological detection," *Nature Biotechnology*, vol. 22, No. 1 (2004), pp. 47-52.

Alleyne, Jr., et al., "Efficacy and biocompatibility of a photopolymerized, synthetic, absorbable hydrogel as a dural sealant in a canine craniotomy model," *J. Neurosurg.*, vol. 88 (1998), pp. 308-313.

Andreopoulos, et al., "Light-induced tailoring of PEG-hydrogel properties," *Biomaterials*, vol. 19 (1998), pp. 1343-1352.

Andrzejewska, et al., "The role of oxygen in camphorquinone-initiated photopolymerization," *Macromol. Chem. Phys.*, vol. 199 (1998), pp. 441-449.

Araujo, et al., "Interaction of Catechol and Gallic Acid with Titanium Dioxide in Aqueous Suspensions. 1. Equilibrium Studies," *Langmuir*, vol. 21 (2005), pp. 3470-3474.

Armstrong et al., "Scanning Microcalorimetric Investigations of Phase Transitions in Dilute Aqueous Solutions of Poly(oxypropylene)," *J. Phys. Chem.*, vol. 99 (1995), pp. 4590-4598.

Arnow, "Colorimetric Determination of the Component of 3, 4-Dihydroxyphemylalanine-Tyrosine Mixtures," *J. Biol. Chem.*, vol. 118 (1937), pp. 531-538.

Arzt et al., "From micro to nano contacts in biological attachment devices," *Proc. Nat. Acad. Sci. USA*, vol. 100 (2003), pp. 10603-10606.

Arzt, "Biological and artificial attachment devices: Lessons for materials scientists from flies and geckos," *Mater. Sci. Eng. C*, vol. 26 (2006), pp. 1245-1250.

Autumn et al., "Adhesive force of a single gecko foot-hair," *Nature*, vol. 405 (2000), pp. 681-685.

Autumn et al., "Evidence for van der Waals adhesion in gecko setae," *Proc. Nat. Acad. Sci. USA*, vol. 99 (2002), pp. 12252-12256.

Baird, et al. (2007), "Reduction of Incisional Cerebrospinal Fluid Leak Following Posterior Foss Surgery with the use of Duraseal," American Association of Neurosurgeons. Abstract retrieved Jul. 23, 2008, from AANS Abstract Center database. Available from: http://www.aans.org/library/article.aspx?ArticleID=42392.

Balsa-Canto, et al., "Reduced-Order Models for Nonlinear Distributed Process Systems and Their Application in Dynamic Optimization," *Ind. Eng. Chem. Res.*, vol. 43 (2004), pp. 3353-3363.

Banerjee, et al., "Derivatives of 3, 4-Dihydroxyphenylalanine for Peptide Synthesis," *J. Org. Chem.*, vol. 41, No. 18 (1976), pp. 3056-3058.

Barbakadze, et al., "Poly[3-(3, 4-dihydroxyphenyl)glyceric Acid], A New Biologically Active Polymer from *Symphytum Asperum Lepech.* and *S. Caucasicum Bieb.* (Boraginaceae)," *Molecules*, vol. 10 (2005), pp. 1135-1144.

Barichello et al., "Absorption of insulin from Pluronic F-127 gels following subcutaneous administration in rats," *Int. J. Pharm.*, vol. 184 (1999), pp. 189-198.

Benedek, "End Uses of Pressure-Sensitive Products" in *Developments in Pressure-Sensitive Products*, Benedek (ed.), CRC Press: Boca Raton, FL (2006). pp. 539-596.

Bharathi, et al., "Direct synthesis of gold nanodispersions in sol-gel derived silicate sols, gels and films," *Chem. Commun.* (1997), pp. 2303-2304.

Bontempo, et al., "Atom Transfer Radical Polymerization as a Tool for Surface Functionalization," *Adv. Mater.*, vol. 14, No. 17 (2002), pp. 1239-1241.

Boogaarts, et al., "Use of a novel absorbable hydrogel for augmentation of dural repair: results of a preliminary clinical study," *Neurosurg.*, vol. 57 (2005), pp. 146-151.

Bromberg, "Novel Family of Thermogelling Materials via C—C Bonding between Poly(acrylic acid) and Poly(ethylene oxide)-*b*-poly(propylene oxide)-*b*-poly(ethylene oxide)," *J. Phys. Chem. B*, vol. 102 (1998), pp. 1956-1963.

Bromberg, "Self-Assembly in Aqueous Solutions of Polyether-Modified Poly(acrylic acid)," *Langmuir*, vol. 14 (1998), pp. 5806-5812.

Bromberg, "Temperature-responsive gels and thermogelling polymer matrices for protein and peptide delivery," *Advanced Drug Reviews*, vol. 31 (1998), pp. 197-221.

Brown, et al., "Micelle and Gel Formation in a Poly(ethylene oxide)/Poly(propylene oxide)/Poly(ethylene oxide) Triblock Copolymer in Water Solution. Dynamic and Static Light Scattering and Oscillatory Shear Measurements," *J. Phys. Chem.*, vol. 95 (1991), pp. 1850-1858.

Bruinsma, et al., "Bacterial adhesion to surface hydrophilic and hydrophobic contact lenses," *Biomaterials*, vol. 22 (2001), pp. 3217-3224.

Bryant, et al., "Cytocompatibility of UV and visible light photoinitiating systems on cultured NIH/3T3 fobroblasts in vitro," *J. Biomater. Sci. Polymer Edn*, vol. 11, No. 5 (2000), pp. 439-457.

Burdick, et al., "Synthesis and Characterization of Tetrafunctional Lactic Acid Oligomers: A potential In Situ Forming Degradable Orthopaedic Biomaterial," *J. Polym. Sci., Part A: Polym. Chem.*, vol. 39 (2001), pp. 683-692.

Burzio, et al., "Cross-Linking in Adhesive Quinoproteins: Studies with Model Decapeptides," *Biochemistry*, vol. 39 (2000), pp. 11147-11153.

Cabana, et al., "Study of the Gelation Process of Polyethylene Oxide$_a$—Polypropylene Oxide$_b$—Polyethylene Oxide$_a$ Copolymer (Poloxamer 407) Aqueous Solutions," *J. Colloid Interface Sci.*, vol. 190 (1997), pp. 307-312.

Campbell, et al., "Evaluation of Absorbable Surgical Sealants: In vitro Testing," Confluent Surgical, Inc. (2005) White Paper. Available from: http://www.confluentsurgical.com/pdf/ds/6070_DuraSeal_Invitro_WP13-25.pdf.

Carmichael, et al., "Selective Electroless Metal Deposition Using Microcontact Printing of Phosphine—Phosophonic Acid Inks," *Langmuir*, vol. 20 (2004), pp. 5593-5598.

Chalykh, et al., "Pressure-Sensitive Adhestion in the Blends of Poly(N-vinyl pyrrolidone) and Poly(ethylene glycol) of Disparate Chain Lengths," *J. of Adhes.*, vol. 78 (2002), pp. 667-694.

Chehimi, et al., "XPS investigations of acid-base interactions in adhesion. Part 3. Evidence for orientation of carbonyl groups from poly(methylmethacrylate) (PMMA) at the PMMA—glass and PMMA—$SiO_2$ interfaces," *J. Electron. Spectrosc. Relat. Phenom.*, vol. 63 (1993), pp. 393-407.

Chen, et al., "Temperature-Induced Gelation Pluronic-g-Poly(acrylic acid) Graft Copolymers for Prolonged Drug Delivery to the Eye," in Harris, et al. (eds.) *Poly(ethylene glycol): Chemistry and Biological Applications*. New York, NY: Oxford University Press USA, 1997. pp. 441-451.

Chen, et al., "Enzymatic Methods for in Situ Cell Entrapment and Cell Release," *Biomacromolecules*, vol. 4 (2003), pp. 1558-1563.

Collier, et al., "Enzymatic Modification of Self-Assembled Peptide Structures with Tissue Transglutaminase," *Bioconjugate Chem.*, vol. 14 (2003), pp. 748-755.

Collier, et al., "Self-Assembling Polymer-Peptide Conjugates: Nanostructural Tailoring," *Adv. Mater.*, vol. 16, No. 11 (2004), pp. 907-910.

Collins, et al., "Use of collagen film as a dural substitute: Preliminary animal studies," *J. Biomed. Mater. Res.*, vol. 25 (1991), pp. 267-276.

Connor, et al., "New Sol—Gel Attenuated Total Reflection Infrared Spectroscopic Method for Analysis of Adsorption at Metal Oxide Surfaces in Aqueous Solutions. Chelation of $TiO_2$, $ZrO_2$, and $Al_2O_3$ Surfaces by Catechol, 8-Quinolinol, and Acetylacetone," *Langmuir*, vol. 11 (1995), pp. 4193-4195.

Cosgrove, et al., "Safety and efficacy of a novel polyethylene glycol hydrogel sealant for watertight dural repair," *J. Neurosurg.*, vol. 106 (2007), pp. 52-58.

Cosgrove, "Safety and Efficacy of a Novel PEG Hydrogel Sealant (DuraSeal®) for Watertight Closure after Dural Repair," Presented at the Congress of Neurological Surgeons 55th Annual Meeting, Boston, MA, Oct. 2005. Available from: http://www.confluentsurgical.com/pdf/ds/CosgroveAbstractCNS2005.pdf.

Crescenzi, et al., "New Gelatin-Based Hydrogels via Enzymatic Networking," *Biomacromolecules*, vol. 3 (2003), pp. 1384-1391.

Creton, "Pressure-Sensitive Adhesives: An Introductory Course," *MRS Bulletin*, vol. 26, No. 6, (2003), pp. 434-439.

Crosby, et al., "Rheological properties and adhesive failure of thin viscoelastic layers," *J. Rheol.*, vol. 46, No. 1 (2002), pp. 273-294.

Crosby, et al., "Controlling Polymer Adhesion with "Pancakes"," *Langmuir*, vol. 21 (2005), pp. 11738-11743.

Cruise, et al., "A Sensitivity Study of the Key Parameters in the Interfacial Photopolymerization of Poly(etheylene glycol) Dlacrylate upon Porcine Islets," *Biotechnol. Bioeng.*, vol. 57, Issue 6 (1998), pp. 655-665.

Dai, et al., "Novel pH-Responsive Amphiphilic Diblock Copolymers with Reversible Micellization Properties," *Langmuir* 19 (2003). pp. 5175-5177.

Dalsin, et al., "Surface Modification for Protein Resistance Using a Biomimetic Approach," *Mat. Res. Soc. Symp. Proc.*, vol. 774 (2002), pp. 75-80.

Dalsin, et al., "Mussel Adhesive Protein Mimetic Polymers for the Preparation of Nonfouling Surfaces," *J. Am. Chem. Soc.* 125 (2003). pp. 4253-4258.

Dalsin, et al., "Antifouling Performance of Poly(ethylene glycol) Anchored onto Surfaces by Mussel Adhesive Protein Mimetic Peptides," *Polymeric Materials Science and Engineering* 90 (2004). pp. 247-248.

Dalsin, et al., "Protein Resistance of Titanium Oxide Surfaces Modified by Biologically Inspired mPEG-DOPA," *Langmuir* 21 (2005). pp. 640-646.

Davis, et al., "Polymeric microspheres as drug carriers," *Biomaterials* 9 (1), 1988. pp. 111-115.

Deible, et al., "Creating molecular barriers to acute platelet deposition on damaged arteries with reactive polyethylene glycol," *J. Biomed. Maters. Res.* 41 (1998). pp. 251-256.

Deming, "Mussel byssus and biomolecular materials," *Current Opinion in Chemical Biology*, 3 (1), 1999. pp. 100-105.

Deming, et al., "Mechanistic Studies of Adhesion and Crosslinking in Marine Adhesive Protein Analogs," *Polym. Mater. Sci. Eng.*, 80 (1999). pp. 471-472.

Deruelle, et al., "Adhesion at the Solid—Elastomer Interface: Influence of the Interfacial Chains," *Macromolecules*, vol. 28 (1995), pp. 7419-7428.

Desai, et al., "In Vitro Evaluation of Pluronic F127-Based Controlled-Release Ocular Delivery Systems for Polocarpine," *J. Phar. Sci.*, 87 (2), 1998. pp. 226-230.

Dillow, et al., "Adhesion of $\alpha_5\beta_1$ receptors to biomimetic substrates constructed from peptide amphiphiles," *Biomaterials*, vol. 22 (2001), pp. 1493-1505.

Donkerwolcke, et al., "Tissue and bone adhesives—historical aspects," *Biomaterials* 19 (1998). pp. 1461-1466.

Dossot, et al., "Role of Phenolic Derivatives in Photopolymerization of an Acrylate Coating," *J. Appl. Polymer. Sci.*, 78 (2000). pp. 2061-2074.

Drumheller, et al., "Polymer Networks with Grafted Cell Adhesion Peptides for Highly Biospecific Cell Adhesive Substrates," *Anal. Biochem.*, vol. 222 (1994), pp. 380-388.

Elbert, et al., "Reduction of fibrous adhesion formation by a copolymer possessing an affinity for anionic surfaces," *J. Biomed. Mater. Res.*, vol. 42, Issue 1 (1998), pp. 55-65.

Elisseeff, et al., "Photoencapsulation of chondrocytes in poly(ethylene oxide)-based semi-interpenetrating networks," *J. Biomed. Mater. Res.*, vol. 51, Issue 2 (2000), pp. 164-171.

Erli, et al., "Surface pretreatments for medical application of adhesion," *BioMed. Eng. Online*, 2 (15), 2003. Available from: http://www.biomedical-engineering-online.com/content/2/2/15.

Fan et al., "Surface-Initiated Polymerization from $TiO_2$ Nanoparticle Surfaces through a Biomimetic Initiator: A New Route toward Polymer-Matrix Composites," *Comp. Sci. Tech.*, 66 (9), 2006. pp. 1195-1201.

Fang, et al., "Effect of Molecular Structure on the Adsorption of Protein on Surfaces with Grafted Polymers," *Langmuir*, vol. 18 (2002), pp. 5497-5510.

Faulkner, et al., "A New Stable Pluronic F68 Gel Carrier for Antibiotics in Contaminated Wound Treatment," *Am. J. Emerg. Med.*, 15 (1), 1997. pp. 20-24.

Feldstein, et al., "Molecular Design of Hydrophilic Pressure-Sensitive Adhesives for Medical Applications," in *Developments in Pressure-Sensitive Products*, I. Benedek (ed.). 2006, CRC Press: Boca Raton, FL. pp. 473-503.

Filpula, et al., "Structural and Functional Repetition in a Marine Mussel Adhesive Protein," *Biotechnol. Prog.* 6 (1990). pp. 171-177.

Fischer, et al., "In vitro cytotoxicity testing of polycations: influence of polymer structure on cell viability and hemolysis," *Biomaterials* 24 (2003). pp. 1121-1131.

Flanigan, et al., "Adhesive and Elastic Properties of Thin Gel Layers," *Langmuir*, vol. 15 (1999), pp. 4966-4974.

Flanigan, et al., "Structural Development and Adhesion of Acrylic ABA Triblock Copolymer Gels," *Macromolecules*, vol. 32 (1999), pp. 7251-7262.

Flood, et al., "Efficient Asymmetric Epoxidation of $\alpha,\beta$-Unstarudated Ketones Using a Soluble Triblock Polyethylene Glycol-Polyamino Acid Catalyst," *Org. Lett.*, vol. 3, No. 5 (2001), pp. 683-686.

Floudas, et al., "Hierarchical Self-Assembly of Poly($\gamma$-benzyl-L-glutamate)—Poly(ethylene glycol)—Poly($\gamma$-benzyl-L-glutamate) Rod—Coil—Rod Triblock Copolymers," *Macromolecules*, vol. 36 (2003), pp. 3673-3683.

Flory, et al., "Effect of Volume Exclusion on the Dimensions of Polymer Chains," *J. Chem. Phys.*, vol. 44, No. 6 (1966), pp. 2243-2248.

Floyd-Smith, et al., "Interferon Action: RNA Cleavage Pattern of a (2'-5')Oligoadenylate-Dependent Endonuclease," *Science*, vol. 212, No. 4498 (May 29, 1981), pp. 1030-1032.

Frank, et al., "Adhesion of *Mytilus edulis* Foot Protein 1 on Silica: Ionic Effects on Biofouling," *Biotechnol. Prog.* 18 (2002). pp. 580-586.

Fuchsbauer, et al., "Influence of gelatin matrices cross-linked with transglutaminase on the properties of an enclosed bioactive material using $\beta$-galactosidase as model system," *Biomaterials* 17 (1996). pp. 1481-1488.

Fujisawa, et al., "Kinetic Evaluations of the Reactivity of Flavonoids as Radical Scavengers," *SAR QSAR Environ. Res.*, Vo. 13, No. 6 (2002), pp. 617-627.

Fuller, et al., "A Procedure for the Facile Synthesis of Amino-Acid N-Carboxyanhydrides," *Biopolymers* 15 (1976). pp. 1869-1871.

Fuller, et al., "DOPA-Containing Polypeptides. I. Improved Synthesis of High-Molecular—Weight Poly (L-DOPA) and Water-Soluble Copolypeptides," *Biopolymers* 17 (1978). pp. 2939-2943.

Geim, et al., "Microfabricated adhesive mimicking gecko foot-hair," *Nat. Materials* 2 (2003). pp. 461-463.

Ghosh, et al., "N,N'-Disuccinimidyl Carbonate: A Useful Reagent for Alkoxycarbonylation of Amines," *Tetra. Lett.* 33 (20), 1992. pp. 2781-2784.

Gidanian, et al., "Redox behavior of melanins: direct electrochemistry of dihydroxyindole-melanin and its Cu and Zn adducts," *J. Inorg. Biochem.* 89 (2002). pp. 54-60.

Green, et al., "A surface plasmon resonance study of albumin adssoption to PEO-PPO-PEO triblock copolymers," *J. Biomed. Res.* 42 (1998). pp. 165-171.

Gross, et al., "Amine Bindindg Sites in Acyl Intermediates of Transglutaminases," *J. Biol. Chem.* 242 (11) (1977). pp. 3752-3759.

Grotenhuis, et al,. "Synthetic Dural Sealant for Prevention of Postoperative CSF Leakage," Presented at the American Association of Neurological Surgeons; Apr. 2003, San Diego, CA. Available from: http://www.confluentsurgical.com/pdf/ds/AbstractGrotenhuisAbstract.pdf.

Grotenhuis, et al., "A Novel Absorbable Hydrogel for Dural Repair: Results of a Pilot Clinical Study," Confluent Surgical, Inc. (2005) White Paper. Available from: http://www.confluentsurgical.com/pdf/ds/DuraSeal_Pilot_Study_WP4-7-05.pdf.

Grotenhuis, "Costs of postoperative cerebrospinal fluid leakage: 1-year, retrospective analysis of 412 consecutive nontrauma cases," *Surg. Neurol.*, vol. 64, No. 6 (2005), pp. 493-494.

Gu, et al., "Synthesis of Aluminum Oxide/Gradient Copolymer Composites by Atom Transfer Radical Polymerization," *Macromolecules* 35 (2002). pp. 8913-8916.

Gu, et al., "The role of microbial biofilms in deterioration of space station candidate materials," *Int. Biodeterioration Biodegradation* 41 (1998). pp. 25-33.

Guvendiren, et al., "Adhesion in Self-Assembled Hydrogels with High DOPA Content," *Proceedings of the 30th Annual Meeting of the Adhesion Society* (2007).

Guvendiren, et al., "Synthesis and Adhesion Properties of DOPA Incorporated Acrylic Triblock Hydrogels," *Proceedings of the 29th Annual Meeting of the Adhesion Society* (2006). pp. 277-279.

Haemers, et al., "Effect of Oxidation Rate on Cross-Linking of Mussel Adhesive Proteins," *Biomacromolecules*, vol. 4 (2003), pp. 632-640.

Hajjaji, et al., "Effect of N-Alkybetaines on the Corrosion of Iron in 1 M HCI Solution," *Corrosion*, vol. 49, No. 4 (1993), pp. 326-334.

Hanawa, et al., "XPS Characterization of the Surface Oxide Film of 316L Stainless Steel Samples that were Located in Quasi-Biological Environments," *Mater. Trans., JIM*, vol. 43, No. 12 (2002), pp. 3088-3092.

Hansen, et al., "Enzymatic Tempering of a Mussel Adhesive Protein Film," *Langmuir* 14 (1998). pp. 1139-1147.

Harris, "Laboratory Synthesis of Polyethylene Glycol Derivatives," *JMS—Rev. Macromol. Chem. Phys.*, vol. C25, No. 3 (1985), pp. 325-373.

Harris (ed.), "Introduction to Biotechnical and Biomedical Applications of Poly(Ethylene Glycol)" in *Poly(Ethylene Glycol) Chemistry: Biotechnical and Biomedical Applications*, Plenum Press: New York, 1992. pp. 1-14.

Hennink, et al., "Novel crosslinking methods to design hydrogels," *Adv. Drug Deliver. Rev.*, vol. 54 (2002), pp. 13-36.

Hern, et al., "Incorporation of adhesion peptides into nonadhesive hydrogels useful for tissue resurfacing," *J. Biomed. Mater. Res.*, vol. 39, Issue 2 (1998), pp. 266-276.

Hillery, et al., "The effect of adsorbed poloxamer 188 and 407 surfactants on the intestinal uptake of 60-nm polystyrene particles after oral administratin in the rat," *Int. J. Pharm.* 132 (1996). pp. 123-130.

Ho, et al., "Nanoseparated Polymeric Networks with Multiple Antimicrobial Properties," *Adv. Mater.* 16 (12), 2004. pp. 957-961.

Hoffman, "Hydrogels for biomedical applications," *Adv. Drug Deliver. Rev.*, vol. 43 (2002), pp. 3-12.

Hohenadl, et al., "Two Adjacent N-terminal Glutamines of BM-40 (Osteonectin, SPARC) Act as Amine Acceptor Sites in Transglutaminase$_c$-catalyzed Modification," *J. Biol. Chem.* 270 (40), 1995. pp. 23415-23420.

Hrkach, et al., "Synthesis of Poly(L-lactic acid-*co*-L-lysine) Graft Copolymers," *Macromolecules*, vol. 28 (1995), pp. 4736-4739.

Hu, et al., "Protection of 3,4-dihydroxyphenylalanine (DOPA) for Fmoc solid-phase peptide synthesis," *Tetra. Lett.* 41 (2000). pp. 5795-5798.

Hu, et al., "Rational Design of Transglutaminase Substrate Peptides for Rapid Enzymatic Formation of Hydrogels," *J. Am. Chem. Soc.*, vol. 125, (2003), pp. 14298-14299.

Huang, et al., "Synthesis and Characterization of Self-Assembling Block Copolymers Containing Adhesive Moieties," *Polym. Prepr.* 42 (2), 2001. pp. 147-148.

Huang, et al., "Synthesis and Characterization of Self-Assembling Block Copolymers Containing Bioadhesive End Groups," *Biomacromolecules* 3 (2002). pp. 397-406.

Huang, et al., "Covalent Attachment of Novel Poly(ethylene glycol)—Poly(DL-lactic acid) Copolymeric Micelles to TiO$_2$ Surfaces," *Langmuir* 18 (2002). pp. 252-258.

Huang, et al., "Functionalization of Surfaces by Water-Accelerated Atom-Transfer Radical Polymerization of Hydroxyethyl Methacrylate and Subsequent Derivatization," *Macromolecules* 35 (2002). pp. 1175-1179.

Huang, et al., "Poly(L-lysine)-*g*-poly(ethylene glycol) Layers on Metal Oxide Surfaces: Surface-Analytical Characterization and Resistance to Serum and Fibrinogen Adsorption," *Langmuir*, vol. 17 (2001), pp. 489-498.

Huang, "Molecular aspects of muco- and bioadhesion: Tethered structures and site-specific surfaces," *J. Controlled Release*, vol. 65 (2000), pp. 63-71.

Huber, et al., "Resolving the nanoscale adhesion of individual gecko spatulae by atomic force microscopy," *Biol. Lett.* 1 (2005). pp. 2-4.

Huber, et al., "Evidence for capillarity contributions to gecko adhesion from single spatula nanomechanical measurements," *Proc. Nat. Acad. Sci. USA*, 102 (45), 2005. pp. 16293-16296.

Huin-Amargier, et al., "New physically and chemically crosslinked hyaluronate (HA)-based hydrogels for cartilage repair," *J. Biomed. Mater. Res.* 76A (2), 2006. pp. 416-424.

Hunter, "Molecular hurdles in polyfectin design and mechanistic background to polycation inducted cytotoxicity," *Adv. Drug Deliver. Rev.*, vol. 58 (2006). pp. 1523-1531.

Hutter, et al., "Calibration of atomic-force microscope tips," *Rev. Sci. Instrum.* 64 (7), Jul. 1993. pp. 1868-1873.

Hvidt, et al., "Micellization and Gelation of Aqueous Solutions of a Triblock Copolymer Studied by Rheological Techniques and Scanning Calorimetry," *J. Phys. Chem.* 98 (1994). pp. 12320-12328.

Hwang, et al., "Expression of Functional Recombinant Mussel Adhesive Protein Mgfp-5 in *Escherichia coli*," *Appl. Environ. Microbiol.* 70 (6), 2004. pp. 3352-3359.

Ikada, "Tissue Adhesives," in *Wound Closure Biomaterials and Devices*, Chu, et al. (eds.), CRC Press, Inc.: Boca Raton, FL, 1997. pp. 317-346.

International Search Report for PCT/US2003/034633; WO 2004/042068 A3 (May 21, 2005); Northwestern University (Applicant); Messersmith, et al. (inventors).

International Search Report for PCT/US2005/006418; WO 2005/118831 A3 (Dec. 15, 2005); Northwestern University (Applicant); Messersmith, et al. (inventors).

International Search Report for PCT/US2005/024642; WO 2006/091226 A3 (Aug. 31, 2006); Northwestern University (Applicant); Messersmith, et al. (inventors).

International Search Report for PCT/US/2005/041280; WO 2006/055531 A3 (May 26, 2006); Northwestern University (Applicant); Messersmith, et al. (Inventors).

International Search Report for PCT/US2007/075299; WO 2008/019352 A3 (Feb. 14, 2008); Nerites Corporation (Applicant); Lee (Inventor).

International Search Report for PCT/US2002/23005; WO 03/008376 A3 (Jan. 30, 2003); Northwestern University (Applicant); Messersmith, et al. (inventors).

Ishihara, et al., "Photocrosslinkable chitosan as a dressing wound occlusion and accelerator in healing process," *Biomaterials*, vol. 23, No. 3 (2002), pp. 833-840.

Jackson, "Tissue sealants: Current status, future potential," *Nat. Med.*, vol. 2, No. 5, (May 1996), pp. 637-638.

Jackson, "Fibrin sealants in surgical practice: An overview," *Am. J. Surg.*, vol. 182 (2001), pp. 1S-7S.

Jänchen, et al., "Adhesion Energy of Thin Collagen Coatings and Titanium," *Surf. Interface Anal.*, vol. 27 (1999), pp. 444-449.

Jensen, et al., "Lipopeptides Incorporated into Supported Phospholipid Monolayers Have High Specific Activity at Low Incorporation Levels," *J. Am. Chem. Soc.*, vol. 126, No. 46 (2004), pp. 15223-15230.

Jeon, et al., "Protein-Surface Interactions in the Presence of Polyethylene Oxide," *J. Colloid. Interface Sci.*, vol. 142, No. 1 (1991), pp. 159-166.

Jewell, et al., "Pharmacokinetics of RheothRx Injection in Healthy Male Volunteers," *J. Phar. Sci.* vol. 86, No. 7 (1997), pp. 808-812.

Jo, et al., "Surface modification using silanated poly(ethylene glycol)s," *Biomaterials*, vol. 21 (2000), pp. 605-616.

Johnson, et al., "Surface Energy and Contact of Elastic Solids," *Proc. R. Soc. Lond.*, A, vol. 324, No. 1558 (1971), pp. 301-313.

Jones, et al., "Controlled Surface-Initiated Polymerization in Aqueous Media," *Adv. Mater.*, vol. 13, No. 16 (2001), pp. 1256-121259.

Jones, et al., "In Situ forming biomaterials," *Oral Maxillofacial Surg. Clin. N. Am.*, vol. 14 (2002), pp. 29-38.

Kacher, et al. "DuraSeal MR and CT Imaging: Evaluation in a Canine Craniotomy Model,", Neurosurgery 58 (1), 140-7 (2006).

Kahlem, et al., "Peptides containing glutamine repeats as substrates for transglutaminase-catalyzed cross-linking: Relevance to diseases of the nervous system," *Proc. Natl. Acad. Sci. USA*, vol. 93 (Dec. 1996), pp. 14580-14585.

Kellaway, et al., "Oral Mucosal Drug Delivery," in *Oral Mucosal Drug Delivery*, Rathbone (ed.). 1996, Marcel Dekkers, Inc.: New York, NY. pp. 221-239.

Kenausis, et al., "Poly(L-lysine)-*g*-Poly(ethylene glycol) Layers on Metal Oxide Surfaces: Attachment Mechanism and Effects on Polymer Architecture on Resistance to Protein Adsoprtion," *J. Phys. Chem. B*, vol. 104 (2000), pp. 3298-3309.

Khudyakov, et al., "Kinetics of Photopolymerization of Acrylates with Functionality of 1-6," *Ind. Eng. Chem. Res.* 38 (1999). pp. 3353-3359.

Kingshott, et al., "Effects of cloud-point grafting, chain length, and density of PEG layers on competitive adsorption of ocular proteins," *Biomaterials* 23 (2002). pp. 2043-2056.

Kirschenbaum, et al., "Sequence-specific polypeptoids: A diverse family of heteropolymers with stable secondary structure," *Proc. NatL Acad. Sci. USA* 95 (1998). pp. 4303-4308.

Kitano, et al., "Resistance of zwitterionic telomers accumulated on metal surfaces against nonspecific adsorption of proteins," *J. Colloid Interface Sci.* 282 (2005). pp. 340-348.

Klug, et al, "In Situ Analysis of Peptidyl DOPA in Mussel Byssus Using Rotational-Echo Double-Resonance NMR," *Arch. Biochem. Biophys.*, vol. 333, No. 1 (Sep. 1, 1996), pp. 221-224.

Kolb, et al., "Click Chemistry: Diverse Chemical Function from a Few Good Reactions," *Agnew. Chem. Int. Ed.*, vol. 40 (2001), pp. 2005-2021.

Koob, et al., "Mechanical and thermal properties of novel polymerized NDGA-gelatin hydrogels," *Biomaterials*, vol. 24 (2003), pp. 1285-1292.

Korobkova, et al., "From molecular noise to behavioural variability in a single bacterium," *Nature* 428 (2004). pp. 574-578.

Kummert, et al., "The Surface Complexation of Organic Acids of Hydrous $\gamma$-$Al_2O_3$," *J. Colloid Interface Sci.*, vol. 75, No. 2 (Jun. 1980), pp. 373-385.

Laucournet, et al., "Catechol derivatives and anion adsorption onto alumina surfaces in aqueous media: influence on the electrokinetic properties," *J. Eur. Ceram. Soc.* 21 (2001). pp. 869-878.

LaVoie, et al., "Dopamine covalently modifies and functionally inactivates parkin," *Nature Med.* 11 (11), 2005. pp. 1214-1221.

Lee, et al., "Enzymatic and Non-Enzymatic Pathways to Formation of DOPA-Modified PEG Hydrogels," *Polymer Preprints* 42 (2), 2001. pp. 151-152.

Lee, et al., "Synthesis and Gelation of DOPA-Modified Poly(ethylene glycol) Hydrogels," *Biomacromolecules* 3 (2002). pp. 1038-1047.

Lee, et al., "Synthesis of 3,4-dihydroxyphenylalanine (DOPA) containing monomers and their co-polymerizations with PEG-diacrylate to form hydrogels," *J. Biomater. Sci. Polymer Edn*, 15 (4), 2004. pp. 449-464.

Lee, et al., "Rapid Gel Formation and Adhesion in Photocurable and Biodegradable Block Copolymers with High DOPA Content," *Macromolecules* 39 (2006). pp. 1740-1748.

Lee, et al., "Biomimetic Adhesive Polymers Based on Mussel Adhesive Proteins," in *Biological Adhesives*, Smith, et al. (eds.), Springer-Verlag: Berlin Heidelberg, 2006. pp. 257-278.

Lee, et al., "Single-Molecule Mechanics of Mussel Adhesion," *Proc. Natl. Acad. Sci. USA*, vol. 103, No. 35 (2006), pp. 12999-13003.

Lee, et al., "Bioadhesive-Based Dosage Forms: The Next Generation," *J. Pharm. Sci.* 89 (7) (2000). pp. 850-866.

Lee, et al., "Hydrogels for Tissue Engineering," *Chem. Rev.*, vol. 101, No. 7 (Jul. 2001), pp. 1869-1879.

Lemieux, et al., "Block and Graft Copolymers and Nanogel™ Copolymer Networks for DNA Delivery into Cell," *J. of Drug Targeting* 8 (2), 2000. pp. 91-105.

Li, et al., "Protein Adsortion on Oligo(ethylene glycol)-Terminated Alkanethiolate Self-Assembled Monolayers: The Molecular Basis for Nonfouling Behavior," *J. Phys. Chem. B* 109 (2005). pp. 2934-2941.

Li, et al., "Copper-Based Metallization for ULSI Applications," *MRS Bulletin* 18 (6), Jun. 1993. pp. 18-21.

Li, et al., "Chemical Modifications of Surface Active Poly(ethylene oxide)—Poly(propylene oxide) Triblock Copolymers," *Bioconj. Chem.* 7 (1996). pp. 592-599.

Li, et al., "Two-Level Antibacterial Coating with Both Release-Killing and Contact-Killing Capabilities," *Langmuir* 22 (24), 2006. pp. 9820-9823.

Long, et al., "A peptide that inhibits hydroxyapatite growth is in an extended conformation on the crystal surface," *Proc. Natl. Acad. Sci. USA* 95 (1998). pp. 12083-12087.

Lorand, et al., "Transglutaminases," *Mol. Cell. Biochem.*, vol. 58 (1984), pp. 9-35.

Love, et al., "Self-Assembled Monolayers of Thiolates on Metals as a Form of Nanotechnology," *Chem. Rev.* 105 (2005). pp. 1103-1169.

Lovich, et al., "Arterial heparin deposition: role of diffusion, convection, and extravascular space," *Am. J. Phsyiol.—Heart C.*, vol. 275 (1998), pp. 2236-2242.

Lu, et al., "Studies on the synthesis and antibacterial activities of polymeric quaternary ammonium salts from dimethylaminoethyl methacrylate," *Reactive & Functional Polymers* 67 (2007). pp. 355-366.

Lucast, "Adhesive considerations for developing stick-to-skin products," *Adhesives Age* 43 (2000). pp. 36, 38-39.

Luo, et al., "Surface-Initiated Photopolymerization of Poly(ethylene glycol) Methyl Ether Methacrylate on a Diethyldithiocarbamate-Mediated Polymer Substrate," *Macromolecules*, vol. 35 (2002), pp. 2487-2493.

Lyman, et al., "Characterization of the formation of interfacially photopolymerized thin hydrogels in contact with arterial tissue," *Biomaterials* 17 (1996). pp. 359-364.

Martin, et al., "Surface Structures of a 4-Chlorocatechol Adsorbed on Titanium Dioxide," *Environ. Sci. Technol.*, vol. 30 (1996), pp. 2535-2542.

Maugh, et al., "Recombinant bioadhesive proteins of marine animals anad their use in adhesive compositions," in Genex Corp. 1988: USA. pp. 196 (1987).

Matyjaszewski, et al., "Atom Transfer Radical Polymerization," *Chem. Rev.* 101 (2001). pp. 2921-2990.

McBride, "Adsorption and Oxidation of Phenolic Compounds by Iron and Manganese Oxides," *Soil Sci. Soc. Am. J.*, vol. 51 (1987), pp. 1466-1472.

McWhitrter, et al., "Siderophore-Mediated Covalent Bonding to Metal (Oxide) Surfaces Biofilm Initiation by *Pseudomonas aeruginosa* Bacteria," *Langmuir*, vol. 19 (2003), pp. 3575-3577.

Meisel, et al., "Estimation of calcium-binding constants of casein phosphopeptides by capillary zone electrophoresis," *Anal. Chim. Acta* 372 (1998). pp. 291-297.

Mellott, et al., "Release of protein from highly cross-linked hydrogels of poly(ethylene glycol) diacrylate fabricated by UV polymerization," *Biomaterials*, vol. 22 (2001), pp. 929-941.

Merrifield, "Solid Phase Peptide Synthesis. I. The Synthesis of a Tetrapeptide," *J. Am. Chem. Soc.*, vol. 85 (Jul. 20, 1963), pp. 2149-2154.

Merrill, "Distinctions and Correspondences among Surfaces Contacting Blood," *Annals of the NY Acad. Sci.* 516 (1987). pp. 196-203.

Miron, et al., "A Simplified Method for the Preparation of Succinimidyl Carbonate Polyethylene Glycol for Coupling to Proteins," *Bioconj. Chem.* 4 (1993). pp. 568-569.

Morgan, et al., "Biochemical characterisation of polycation-induced cytotoxicity to human vascular endothelial cells," *Journal of Cell Science* 94(3), 1989,. pp. 553-559.

Morikawa, "Tissue sealing," *Am. J. Surg.*, vol. 182 (2001), pp. 29S-35S.

Mougin, et al., "Construction of Cell-Resistant Surfaces by Immobilization of Poly(ethylene glycol) on Gold," *Langmuir*, vol. 20 (2004), pp. 4302-4305.

Mowery, et al., "Adhesion of Thermally Reversible Gels to Solid Surfaces," *Langmuir*, vol. 13 (1997), pp. 6101-6107.

Mrksich, et al., "Using Self-Assembled Monolayers that Present Oligo(ethylene glycol) Groups to Control the Interactions of Proteins with Surfaces," *American Chemical Society Symposium Series on Chemistry and Biological Applications of Polyethylene Glycol*, vol. 680 (1997), pp. 361-373.

Mukkamala, et al., "Hydrogel Polymers from Alkylthio Acrylates for Biomedical Applications," *Polymer Gels: Fundamentals and Applciations* 833 (2003). pp. 163-174.

Müller, et al., "Interaction of differentiated HL60 cells with poloxamer and poloxamine surface modified model drug carriers," *Eur. J. Phar. Sci.* 5 (1997). pp. 147-153.

Nakagawa, et al., "ENH, Containing PDZ and LIM Domains, Heart/Skeletal Muscle-Specific Protein, Associates with Cytoskeletal Proteins through the PDZ Domain," *Biocehm. Biophys. Res. Commun.* 272 (2000). pp. 505-512.

Nakayama, et al., "Newly Designed Hemostatic Technology Based on Photocurable Gelatin," *ASAIO J.*, vol. 41, No. 3 (1995), pp. M374-M378.

Nakayama, et al., "Photocurable Surgical Tissue Adhesive Glues Composed of Photoreactive Gelatin and Poly(ethylene glycol) Diacrylate," *J. Biomed. Mater. Res.*, vol. 48, Issue 4 (1999), pp. 511-521.

Nakayama, et al., "Development of high-performance stent: gelatinous photogel-coated stent that permits drug delivery and gene transfer," *J. Biomed. Mater. Res.*, vol. 57, Issue 4 (2001), pp. 559-566.

Nakonieczna, et al., "A New Convenient Route for the Synthesis of DOPA Peptides," *Liebigs Annalen der Chemie*, Issue 10 (1994). pp. 1055-1058.

Neff, et al., "A novel method for surface modification to promote cell attachment to hydrophobic substrates," *J. Biomed. Mater. Res.* 40 (1998). pp. 511-519.

Ninan, et al., "Adhesive strength of marine mussel extracts on porcine skin," *Biomaterials* 24 (2003). pp. 4091-4099.

Nishiyama, et al., "Effects of a strucutural change in collagen upon binding to conditioned dentin studied by $^{13}$C NMR," *J. Biomed. Mater. Res.*, vol. 29 (1995), pp. 107-111.

Nishiyama, et al., "Adhesion mechanisms of resin to etched dentin primed with N-methacryloyl glycine studied by $^{13}$C-NMR," *J. Biomed. Mater. Res.*, vol. 40 (1998). pp. 458-463.

Nishiyama, et al., "Adhesion of N-Methacryloyl-ω-Amino Acid Primers to Collagen Analyzed by $^{13}$C NMR," *J. Dent. Res.*, vol. 80, No. 3 (2001), pp. 855-859.

Northen, et al., "A batch fabricated biomimetic dry adhesive," *Nanotechnology* 16 (8), 2005. pp. 1159-1166.

Northen, et al., "Meso-scale adhesion testing of integrated micro- and nano-scale structures," *Sensors and Actuators A* 130-131 (2006). pp. 583-587.

Nyström, et al., "Dynamic Light Scattering and Rheological Studies of Thermoreversible Gelation of a Poly(ethylene oxide)-Poly(propylene oxide)-Poly(ethylene oxide) Triblock Copolymer in Aqueous Solution," *Faraday Discuss.* 101 (1995). pp. 335-344.

Nyström, et al., "Dynamic Viscoelasticity of an Aqueous System of a Poly(ethylene oxide)—Poly(propylene oxide)—Poly(ethylene oxide) Triblock Copolymer during Gelation," *J. Phys. Chem.* 100 (1996). pp. 5433-5439.

O'Keefe, et al., "Poloxamer-188 as an Adjunct to Primary Percutaneous Transluminal Coronary Angioplasty for Acute Myocardial Infarction," *Am. J. Cardiol.* 78 (1996). pp. 747-750.

Okino, et al., "In situ hydrogelation of photocurable gelatin and drug release," *J. Biomed. Mater. Res.*, vol. 59, Issue 2 (2001), pp. 233-245.

Online Medical Dictionary. "Amino acid." Available from: http//cancerweb.ncl.ac.uk/cgi-bin/omd?query=amino+acid, (Nov. 13, 1997).

Ono, et al., "Photocrosslinkable chitosan as a biological adhesive," *J. Biomed. Mater. Res.*, vol. 49, Issue 2 (1999), pp. 289-295.

Ooka, et al., "Surface-Enhanced Raman Spectroscopy of DOPA-Containing Peptides Related to Adhesive Protein of Marine Mussel, *Mytilus edulis*," *Biopolymers (Biospectroscopy)*, vol. 57, Issue 2 (2000), pp. 92-102.

Orban, et al., "Cytomimetic Biomaterials. 4. In-Situ Photopolymerization of Phospholipids on an Alkylated Surface," *Macromolecules* 33 (2000). pp. 4205-4212.

Ostuni, et al., "A Survey of Structure—Property Relationships of Surfaces that Resist the Adsorption of Protein," *Langmuir* 17 (2001). pp. 5605-5620.

Palmer, et al., "Surfactant Administration Reduces Testicular Ischemia-Reperfusion Injury," *J. Urol.* 159 (1998). pp. 2136-2139.

Papov, et al., "Hydroxyarginine-containing Polyphenolic Proteins in the Adhesive Plaques of the Marine Mussel *Mytilus edulis*," *J. Biol. Chem.* 270 (34) (1995). pp. 20183-20192.

Pardo, et al., "Purification of Adhesive Proteins from Mussels," *Protein Expression and Purif.* 1 (2), 1990. pp. 147-150.

Parsons, "Characteristics of the amino acids as components of a peptide hormone sequence," in *Peptide Hormones*, University Park Press: 1976. pp. 1-7.

Pasche, et al., "Effects of Ionic Strength and Surface Charge on Protein Adsorption at PEGylated Surfaces," *J. Phys. Chem. B* 109 (2005). pp. 17545-17552.

Patel, et al., "Synthesis of Benzyl Esters of α-Amino Acids," *J. Org. Chem.* 30 (1965). pp. 3575-3576.

Peressadko, et al, "When Less is More: Experimental Evidence for Tenacity Enhancement by Division of Contact Area," *J. Adhes.* 80 (2004). pp. 247-261.

Perruchot, et al., "Synthesis of Well-Defined, Polymer-Grafted Silica Particles by Aqueous ATRP" *Langmuir*, vol. 17 (2001), pp. 4479-4481.

Pierpont, et al, "Transition Metal Complexes of *o*-Benzoquinone, *o*-Semiquinone, and Catecholate Liqands," *Coord. Chem. Rev.*, vol. 38 (1981), pp. 45-87.

Preul, et al., "Use of a Novel Hydrogel Sealant in a Canine Dural Repair Model," Presented at the American Association of Neurological Surgeons; Apr. 2002, Chicago, IL. Available from: http://www.confluentsurgical.com/pdf/ds/Abstract0BNI_PreulAbstract.pdf.

Preul, et al., "Obtaining Watertight Closures of Duraplasty Onlay Grafts in a Craniotomy Preclinical Model," Confluent Surgical, Inc. (2005), 'White Paper.' Available from: http://www.confluentsurgical.com/pdf/LT-6000-034RevA-DuraSeal_duraplasty_study_white_paper.pdf.

Prime, et al., "Adsorption of Proteins onto Surfaces Containing End-Attached Oligo(ethylene oxide): A Model System Using Self-Assembled Monolayers," *J. Am. Chem. Soc.* 115 (1993). pp. 10714-10721.

Prucker, et al., "Polymer Layers through Self-Assembled Monolayers of Initiators," *Langmuir*, vol. 14 (1998), pp. 6893-6898.

Pyun, et al., "Synthesis of Polymer Brushes Using Atom Transfer Radical Polymerization," *Macromol. Rapid. Commun.* 24 (2003). pp. 1043-1059.

Rajh, et al., "Surface Restructuring of Nanoparticles: An Efficient Route for Ligand-Metal Oxide Crosstalk," *J. Phys. Chem. B*, vol. 106 (2002), pp. 10543-10552.

Ramakrishna, et al., "Effect of Particle Size on the Reactivity of Quantum Size ZnO Nanoparticles and Charge-Transfer Dynamics with Adsorbed Catechols," *Langmuir*, vol. 19 (2003), pp. 3006-3012.

Ranger, et al., "Pneumostasis of Experimental Air Leaks with a New Photopolymerized Synthetic Tissue Sealant," *Am. Surg.*, vol. 63, Issue 9 (1997), pp. 788-795.

Reed, et al., "A One-Step Synthesis of Monoprotected Polyethylene Glycol Ethers," *J. Org. Chem.*, vol. 65 (2000), pp. 5843-5845.

Rodríguez, et al., "Surface Complexation at the $TiO_2$ (anatase)/Aqueous Solution Interface: Chemisorption of Catechol," *J. Colloid Interface Sci.*, vol. 177 (1996), pp. 122-131.

Rodríguez-Hernández, et al., "High Branched Poly(L-lysine)," *Biomacromolecules*, vol. 4 (2003), pp. 249-258.

Ross-Murphy, "Rheological Characterization of Polymer Gels and Networks," *Polym. Gels Networks*, vol. 2 (1994), pp. 229-237.

Rozier, et al., Gelrite®: A novel, ion-activated, in situ gelling polymer for ophthalmic vehicles. Effect on bioavailability of timolol, *Int. J. Pharm.* 57 (2), 1989. pp. 163-168.

Ruel-Gariépy, et al., "In situ-forming hydrogels—review of temperature-sensitive systems," *Eur. J. Pharm. Biopharm.* 58 (2004). pp. 409-426.

Ruibal, et al., "The Structure of the Digital Setae of Lizards," *J. Morph.* 117 (1965). pp. 271-294.

Ryu, et al., "A Generalized Approach to the Modification of Solid Surfaces," *Science* 308 (2005). pp. 236-239.

Rzepecki, et al., "α,β-Dehydro-3,4-dihydroxyphenylalanine Derivatives: Potential Schlerozation Intermediates in Natural Composite Materials," *Arch. Biochem. Biophys.* 285 (1) (1991). pp. 17-26.

Rzepecki, et al., "Wresting the muscle from mussel beards: research and applications," *Mol. Mar. Biol. Biotech.* 4 (4) (1995). pp. 313-322.

Rzepecki, et al., "Bioadhesives: DOPA and Phenolic proteins as components of organic composite materials", *Principles of Cell Adhesion*, P.D. Richardson and M. Steiner (eds.), CRC Press, Boca Raton, FL. (1995). pp. 107-142142.

Saby, et al., "*Mytilus edulis* Adhesive Protein (MAP) as an Enzyme Immobilization Matrix in the Fabrication of Enzyme-Based Electrodes," *Electroanalysis* 10 (17) (1998). pp. 1193-1199.

Sanborn, et al., "In situ crosslinking of a biomimetic peptide-PEG hydrogel via thermally triggered activation of factor XIII," *Biomaterials*, vol. 23 (2002), pp. 2703-2710.

Sawada, et al., "Micropatterning of Copper on a Poly(ethylene terephthalate) Substrate Modified with a Self-Assembled Monolayer," *Langmuir* 22 (2006). pp. 332-337.

Sawhney, et al., "Interfacial photopolymerization of poly(ethylene glycol)-based hydrogels upon alginate-poly(*l*-lysine) microcapsules for enhanced biocompatibility," *Biomaterials*, vol. 14, No. 13 (1993), pp. 1008-1016.

Sawhney, et al., "Bioerodible Hydrogels Based on Photopolymerized Poly(ethylene glycol)-*co*-poly(α-hydroxy acid) Diacrylate Macromers," *Macromolecules*, vol. 26 (1993), pp. 581-587.

Schmolka, "Articifial Skin. I. Preparation and Properties of Pluronic F-127 Gels for Treatment of Burns," *J. Biomed. Mater. Res.* 6 (6) (1972). pp. 571-582.

Schnurrer, et al., "Mucoadhesive properties of the mussel adhesive protein," *Int. J. Pharm.* 141 (1996). pp. 251-256.

Sever, et al., "Synthesis of peptides containing DOPA (3.4-dihydroxyphenylalanine)," *Tetrahedron* 57 (2001). pp. 6139-6146.

Sever, et al., "Metal-Mediated Cross-Linking in the Generation of a Marine-Mussel Adhesive," *Angew. Chem. Int. Ed.*, vol. 43 (2004), pp. 448-450.

Shull, et al., "Fracture Mechanics Studies of Adhesion in Biological Systems," *Interface Sci.*, vol. 8 (2000), pp. 95-110.

Shull, "Contact mechanics and the adhesion of soft solids," *Mater. Sci. Eng., R* 36 (2002). pp. 1-45.

Sichel, et al., "Relationship Between Melanin Content and Superoxide Dismutase (SOD) Activity in the Liver of Various Species of Animals," *Cell Biochem. Funct.* 5 (1987). pp. 123-128.

Sierra, "Fibrin Sealant Adhesive Systems: A Review of Their Chemistry, Material Properties and Clinical Applications," *J. Biomed. Appl.*, vol. 7 (1993), pp. 309-352.

Sitti, et al., "Synthetic Gecko Foot-Hair Micro/Nano-Structures as Dry Adhesives," *J. Adhes. Sci. Technol.*, vol. 17, No. 8 (2003), pp. 1055-1073. Available from: http://nanolab.me.cmu.edu/publications/papers/Sitti-JAST2003.pdf.

Skelhorne, et al., "Hydrogel Adhesives for Wound-Care Applications," *Medical Device Technology* (Nov. 2002). pp. 19-23.

Soriaga, et al., "Determination of the Orientation of Adsorbed Molecules at Solid-Liquid Interfaces by Thin-Layer Electrochemistry: Aromatic Compounds at Platinum Electrodes," *J. Am. Chem. Soc.* 104 (1982). pp. 2735-2742.

Sousa, et al., "Human Serum Albumin Adsorption on $TiO_2$ from Single Protein Solutions and from Plasma," *Langmuir*, vol. 20 (2004), pp. 9745-9754.

Sperinde, et al., "Synthesis and Characterization of Enzymatically-Cross-Linked Poly(ethylene glycol) Hydrogels," *Macromolecules* 30 (18) (1997). pp. 5255-5264.

Sperinde, et al., "Control and Prediction of Gelation Kinetics in Enzymatically Cross-Linked Poly(ethylene glycol) Hydrogels," *Macromolecules* 33 (2000). pp. 5476-5480.

Spolenak, et al., "Adhesion design maps for bio-inspired attachment systems," *Acta. Biomater.* 1 (2005). pp. 5-13.

Spotnitz, "History of Tissue Adhesives." In: Sierra, et al. (eds.), *Surgical Adhesives and Sealants: Current Technology and Applications*. Technomic Publishing Company, Inc.: Lancaster, PA (1997). pp. 3-11.

Spotnitz, "Commercial fibrin sealants in surgical care," *Am. J. Surg.* 182 (2001). pp. 8S-14S.

Stevens, "Trace bio-organic constituents of gelatins—a review," *Food Australia*, vol. 44, No. 7 (1992), pp. 320-324.

Stile, et al., "Sequential robust design methodology and X-ray photoelectron spectroscopy to analyze the grafting of hyaluronic acid to glass substrates," *J. Biomed. Mater Res.*, vol. 61, Issue 3 (2002), pp. 391-398.

Stiles, et al., "Axisymmetric Adhesion Test to Examine the Interfacial Interactions between Biologically-Modified Networks and Models of the Extracellular Matrix," *Langmuir*, vol. 19 (2003), pp. 1863-1860.

Strausberg, et al., "Protein-based medical adhesives," *Trends in Biotechnology* 8 (2) (1990). pp. 53-57.

Strausberg, et al., "Development of a microbial system for production of mussel adhesive protein." In: *Adhesives from Renewable Resources*. Hemingway, et al. (eds.), ACS Symposium Series 385, American Chemical Society, Washington, D.C. (1989). pp. 453-464.

Sugumaran, et al., "Chemical- and Cuticular Phenoloxidase-Mediated Synthesis of Cysteinyl-Catechol Adducts," *Arch. Insect Biochem. Physiol.* 11 (2) (1989). pp. 127-137.

Sugumaran, "Unified Mechanism for Sclerotization of Insect Cuticle," *Adv. Insect. Physiol.*, vol. 27 (1998), pp. 229-334.

Sun, et al., "Improved antifouling property of zwitterionic ultrafiltration membrane composed of acrylonitrile and sulfobetaine copolymer," *J. of Memr. Sci.* 285 (2006). pp. 299-305.

Sun, et al., "The Nature of the Gecko Lizard Adhesive Force," *Biophys. J.* 89 (2005). pp. L14-L16.

Swerdloff, et al., "Solid phase synthesis of bioadhesive analogue peptides with trifluoromethanesulfonic acid cleavage from PAM resin," *Int. J. Peptide Protein Res.*, vol. 33 (1989), pp. 318-327.

Tae, et al., "Sustained release of human growth hormone from in situ forming hydrogels using self-assembly of fluoroalkyl-ended poly-(ethylene glycol)," *Biomaterials*, vol. 26 (2005), pp. 5269-5266.

Taira, et al., "Analysis of Photo-iniators in Visible-light-cured Dental Composite Resins," *J. Dent. Res.*, vol. 67, No. 1 (1988), pp. 24-28.

Tan, et al., "Surface modification of nanoparticles by PEO/PPO block copolymers to minimize interactions with blood components and prolong blood circulation in rats," *Biomaterials*, vol. 14, No. 11 (1993), pp. 823-833.

Tatehata, et al., "Model Polypeptide of Mussel Adhesive Protein. I. Synthesis and Adhesive Studies of Sequential Polypeptides (X-Tyr-Lys)$_n$ and (Y-Lys)$_n$," *J. Appl. Polym. Sci.*, vol. 76, No. 6 (2000), pp. 929-937.

Taylor, et al., "Polargraphic and Spectrophotometric Investigation of Iron(III) Complexation to 3,4-Dihydroxyphenylalanine-Containing Peptides and Proteins from *Mytilus edulis*," *Inorg. Chem.*, vol. 33 (1994), pp. 5819-5824.

Taylor, et al., "*trans*-2,3-*cis*-3,4-Dihydroxyproline, a New Naturally Occurring Amino Acid, Is the Sixth Residue in the Tandemly Repeated Consensus Decapeptides of an Adhesive Protein from *Mytilus edulis*," *J. Am. Chem. Soc.*, vol. 116 (1994), pp. 10803-10804.

Taylor, et al., "Ferric Ion Complexes of a DOPA-Containing Adhesive Protein from *Mytilus edulis*," *Inorg. Chem.*, vol. 35 (1996), pp. 7572-7577.

Uyama, et al., "Surface Modification of Polymers by Grafting," *Advances in Polymer Science*, vol. 137 (1998), pp. 1-39.

Venkatraman, et al., "Skin adhesives and skin adhesion. 1. Transdermal drug delivery systems," *Biomaterials*, vol. 19 (1998), pp. 1119-1136.

Vörös, et al., "Optical grating coupler biosensors," *Biomaterials*, vol. 23 (2002), pp. 3699-3710.

Waite, "Evidence for a Repeating 3,4-Dihydroxyphenylalanine- and Hydroxyproline-containing Decapeptide in the Adhesive Protein of the Mussel, *Mytilus edulis* L.," *J. Biol. Chem.*, vol. 258, No. 5 (1983), pp. 2911-2915.

Waite, et al., "Assay of Dihdroxyphenylalanine (Dopa) in Invertebrate Structural Proteins," *Methods Enzymol.*, vol. 107 (1984), pp. 397-413.

Waite, "Adhesion à la Moule," *Integr. Comp. Biol.*, vol. 42 (2002), pp. 1172-1180.

Waite, "Mussel Beards: A Coming of Age" *Chem. Ind.* (Sep. 2, 1991), pp. 607-611.

Waite, "Nature's underwater adhesive specialist," *Int. J. Adhes. Adhes.*, vol. 7, No. 1 (1987), pp. 9-14.

Waite, "Nature's underwater adhesive specialist," *Chemtech*, vol. 17 (1987), pp. 692-697.

Waite, et al., "3,4-Dihydroxyphenylalanine in an Insoluble Shell Protein of *Mytilus edulis*," *Biochem. Biophys. Acta*, vol. 541 (1978), pp. 107-114.

Waite, et al., "Polyphosphoprotein from the Adhesive Pads of *Mytilus edulis*," *Biochemistry*, vol. 40 (2001) pp. 2887-2893.

Waite, et al., "The Bioadhesive of *Mytilus byssus*: A Protein Containing L-DOPA," *Biochem. & Biophy. Res. Comm.*, vol. 96, No. 4 (1980), pp. 1554-1561.

Waite, et al., "Mussel Adhesion: Finding the Tricks Worth Mimicking," *J. Adhes.*, vol. 81 (2005), pp. 297-317.

Waite, et al., "Polyphenolic Substance of *Mytilus edulis*: Novel Adhesive Containing L-Dopa and Hydroxyproline," *Science*, vol. 212, No. 4498 (1981), pp. 1038-1040.

Waite, "Precursors of Quinone Tanning: Dopa-Containing Proteins," *Methods Enzymol.*, vol. 258 (1995), pp. 1-21.

Wang, et al., "Facile synthesis of well-defined water-soluble polymers via atom transfer radical polymerization in aqueous media at ambient temperature," *Chem. Commun.* (1999), pp. 1817-1818.

Wang, et al., "Facile Atom Transfer Radical Polymerization of Methoxy-Capped Oligo(ethylene glycol) Methacrylate in Aqueous Media at Ambient Temperature," *Macromolecules*, vol. 33 (2000), pp. 6640-6647.

Wanka, et al., "The aggregation behavior of poly-(oxyethylene)-poly-(oxypropylene)-poly-(oxyethylene)-block-copolymers in aqueous solution," *Cooloid. Polym. Sci.*, vol. 268 (1990), pp. 101-117.

Warner, et al., "Expression of multiple forms of an adhesive plaque protein in an individual mussel, *Mytilus edulis*," *Mar. Biol.*, vol. 134 (1999), pp. 729-734.

Watanabe, et al., "Bonding durability of photocured phenyl-P in TEGDMA to smear layer-retained bovine dentin," *Quint. Int.*, vol. 24, No. 5 (1993), pp. 335-342.

Webber, et al., "Effects of geometric confinement on the adhesive debonding of soft elastic solids," *Phys. Rev. E*, vol. 68 (2003), pp. 021805-1-to-021805-11.

Whitesides, "The origins and the future of microfluidics," *Nature*, vol. 442 (2006), pp. 368-373.

Wisniewski, et al., "Methods for reducing biosensor membrane biofouling," *Colloids Surf., B*, vol. 18 (2000), pp. 197-219.

Yamada, "Chitosan Based Water-Resistant Adhesive. Analogy to Mussel Glue," *Biomacromolecules*, vol. 1 (2000), pp. 252-258.

Yamamoto, "Marine Adhesive Proteins and Some Biotechnological Applications," *Biotechnol. Genet. Eng. Rev.*, vol. 13 (1996), pp. 133-165.

Yamamoto, "Adhesive studies of synthetic polypeptides: A model for marine adhesive proteins," *J. Adhesion Sci. Tech.*, vol. 1, No. 2 (1987), pp. 177-183.

Yamamoto, "Synthesis and Adhesive Studies of Marine Polypeptides," *J. Chem. Soc. Perkin Trans.*, vol. 1 (1987), pp. 613-618.

Yamamoto, "Insolubilizing and adhesive studies of water-soluble synthetic model proteins," *Int. J. Biol. Macromol.*, vol. 12 (1990), pp. 305-310.

Yamamoto, et al., "Synthesis and Adhesives of Marine Adhesive Proteins of the Chilean Mussel *Aula comya ater*," *Biomimetics*, vol. 1, No. 3 (1992), pp. 219-238.

Yamamoto, et al., "Work of Adhesion of Synthetic Polypeptides Containing *L*-Lysine," *J. Colloid Interface Sci.*, vol. 156 (1993), pp. 515-517.

Yamamoto, et al., "Wettability and Adhesion of Synthetic Marine Adhesive Proteins and Related Model Compounds," *J. Colloid Interface Sci.*, vol. 176 (1995), pp. 111-116.

Yang, et al., "Physicochemical aspects of drug delivery and release from polymer-based colloids," *Curr. Opin. Colloid Interface Sci.*, vol. 5 (2000), pp. 132-143.

Young, et al., "Marine Animals and Adhesion." In: Allen (ed.), *Adhesion 6*. Applied Science Publishers: London and New Jersey, 1982. pp. 19-39.

Yu, et al., "Micellisation and Gelation of Triblock Copoly(oxyethylene/oxypropylene/oxyethylene), F127," *J. Chem. Soc., Faraday Trans.*, vol. 88, No. 17 (1992), pp. 2537-2544.

Yu, et al., "Synthetic Polypeptide Mimics of Marine Adhesives," *Macromolecules*, vol. 31 (1998), pp. 4739-4745.

Yu, et al., "Role of L-3,4-Dihydroxyphenylalanine in Mussel Adhesive Proteins," *J. Am. Chem. Soc.*, vol. 121 (1999), pp. 5825-5826.

Yurdumakan, et al., "Synthetic gecko foot-hairs from multiwalled carbon nanotubes," *Chem. Commun.*, vol. 30 (2005), pp. 3799-3801.

Zekorn, et al., "Biocompatibility and immunology in the encapsulation of islets of Langerhans (bioartificial pancreas)," *Int J. Artif. Organs*, vol. 19, No. 4 (1996), pp. 251-257.

Zeng, et al., "Synthesis and Characterization of DOPA-PEG Conjugates," *Polymer Preprints*, vol. 41, No. 1 (2000), pp. 989-990.

Zhan, et al., "Functionalization of Nano-Faujasite Zeolite with PEG-Grafted PMA Tethers Using Atom Transfer Radical Polymerization," *Macromolecules*, vol. 37 (2004), pp. 2748-2753.

Zhao, et al., "Polymer brushes: surface-immobilized macromolecules," *Prog. Polym. Sci.*, vol. 25 (2000), pp. 677-710.

Zuckermann, et al., "Efficient Method for the Preparation of Peptoids [Oligo(N-substituted glycines)] by Submonomer Solid-Phase Synthesis," *J. Am. Chem. Soc.*, vol. 114 (1992), pp. 10646-10647.

* cited by examiner

PEPTIDOMIMETIC POLYMERS FOR ANTIFOULING SURFACES

CROSS-REFERENCE TO RELATED APPLICATIONS

This application claims priority to U.S. Ser. No. 10/199,960 filed Jul. 19, 2002 which claimed priority to U.S. Ser. Nos. 60/306,750 and 60/373,919 filed, respectively, on Jul. 20, 2001 and Apr. 29, 2002. This application also claims priority to U.S. Ser. No. 60/548,314 filed Feb. 27, 2004, U.S. Ser. No. 60/549,259 filed Mar. 2, 2004. This application is also a continuation-in-part of U.S. Ser. No. 11/068,298 filed Feb. 27, 2005, U.S. Ser. No. 60/586,742, filed Jul. 9, 2004, U.S. Ser. No. 11/179,218, filed Jul. 11, 2005 and U.S. Ser. No. 60/628,359, filed Nov. 16, 2004.

STATEMENT REGARDING FEDERALLY SPONSORED RESEARCH OR DEVELOPMENT

The United States government has certain rights to this invention pursuant to Grant No. DE14193 from the National Institute of Health to Northwestern University.

BACKGROUND OF THE INVENTION

Protein, cell, and bacterial fouling of surfaces occur spontaneously upon exposure of medical implants and diagnostic devices to physiologic fluids and tissues. In many cases biofouling is an adverse event that can impair function or even cause catastrophic failure of medical devices. Examples of problematic biofouling include occlusion of cardiovascular implants by thrombus, protein accumulation onto biosensor surfaces, and bacterial colonization of indwelling catheters. Complications arising from fouling of medical implants and devices significantly increase the cost of healthcare delivery and can lead to reduction of implant performance, implant failure, and patient infections.

Strategies in the art for inhibiting biofouling are directed to grafting antifouling polymers or self-assembled monolayers (SAMs) onto surface. Technical issues critical to the longevity and antifouling performance of such organic coatings include the nature of the chemical bond used for anchoring such coatings onto surfaces, as well as the chemical characteristics of the polymer/SAM. Common anchoring chemistries include thiol- and silane-containing molecules on metals and metal oxides, respectively, electrostatic interactions between polyelectrolytes and charged surfaces, and numerous strategies that take advantage of reactive organic functional groups on surfaces and molecules in solution or the vapor phase. While oligoethylene glycol terminated SAMs have shown excellent antifouling properties, their stability under in-vivo conditions may be limited in certain applications. A variety of polymers have been investigated as antifouling coatings, including poly(ethylene glycol) (PEG), poly(methoxyethyl acrylate) (PMEA), poly(phosphorylcholine methacrylate), and glycomimetic polymers. Each of these polymers has met with some success in in-vitro and in-vivo antifouling tests. However, none have yet proven to be ideal for long-term prevention of protein, cell, and bacterial fouling of surfaces.

BRIEF SUMMARY OF THE INVENTION

Briefly, in one aspect, the present invention comprises macromolecular, antifouling, chimeric compositions or coatings comprising a peptide or polypeptide anchor moiety or component coupled to a peptoid or polypeptoid moiety or component. A peptoid moiety of this invention is generally resistant to, or inhibits, protein adsorption or cell fouling of surfaces onto which the composition is coated or attached. Generally speaking the compositions of this invention are referred to as peptidomimetic or chimeric polymers and comprise coupled anchor and peptoid moieties of the following structure:

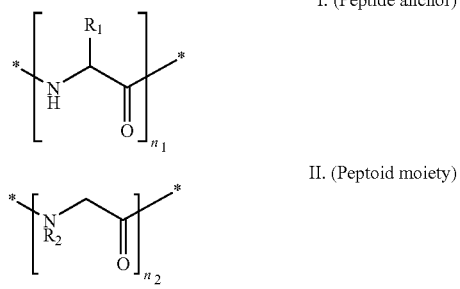

wherein $R_1$ is at least one dihydroxyphenyl derivative (DHPD) alone or in combination with amine-terminated lower alkyl chains having from 1 to about 10 carbon atoms (preferably about 1 to about 7 carbon atoms). The lower alky structures of this invention may be branched or unbranched, saturated or unsaturated and contain minor heteroatom (generally O, N, or S,) constituents which do not materially alter the alkyl chain properties. The alkyl structure need not all have the same number of carbon atoms or the same structure. The DHPD's also may be the same or different;

$R_2$ has at least one ether (C—O—C) linkage (multiple ether linkages are contemplated) and comprises ether-linked alkyl groups or chains, each having from 1 (i.e., $CH_3$—O—$CH_2$—) to about 10 carbon atoms, preferably from 1 to about 7 carbon atoms, and being uncharged, branched, unbranched, saturated or unsaturated;

$n_1$ has a value in the range of about 1 to about 10, preferably 1 to about 8 and most preferably 2 to about 6; and $n_2$ has a value in the range of about 5 to about 100 or more, preferably about 8 to about 50, and more preferably about 10 to about 30.

A general preparative route for the coupled moieties of this invention, i.e., the peptidomimetic composition or coating, is shown in Scheme 1, as follows:

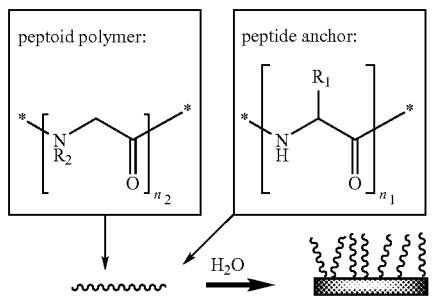

Scheme 1 shows the general synthetic route for peptidomimetic compositions of the invention as well as a schematic showing of a peptidomimetic coated surface (greatly magnified) of this invention.

The general design of such chimeric polymers of this invention can be described in a preferred aspect as a functional peptide domain component for robust adsorption deposition, adhesive, absorptive, or other interaction with surfaces, coupled or conjugated to an N-substituted glycine peptoid polymer component that is resistant to protein and cell fouling. The synthetic approach is versatile and allows virtually unlimited variation of composition. Modification of a variety of surfaces can be accomplished with a simple aqueous solution-based adsorption or deposition strategy. In certain embodiments, a peptidomimetic polymer of this invention can be adsorbed to, or deposited on, a metal oxide surface (e.g., titanium oxide), which in turn exhibits significantly reduced serum protein adsorption, and inhibited cell fouling for weeks, months, to several months (or longer) under in-vitro conditions.

The preferred class of anchoring peptide domain or moiety was chosen to mimic the adhesive proteins used by marine mussels to attach to underwater surfaces. Mussels are known for their ability to adhere strongly to a variety of wet surfaces, and for this purpose secrete liquid "glues" containing mussel adhesive proteins (MAPs), which rapidly harden to form a solid adhesive plaque.

In one aspect, the adhesive or anchor moiety of a composition of this invention comprises dihydroxyphenyl derivatives (DHPD) including, di-(DHPD) wherein the second DHPD is

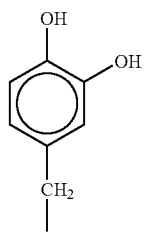

i.e., a methylene derivative of dihydroxyphenyl. A preferred DHPD is L, 3, 4 dihydroxyphenyl alanine (DOPA) which is more completely described below.

In a further preferred practice the adhesive moiety comprises DHPD including a pendent chain comprising ethylenic or vinylic unsaturation such as, for example, an alkyl acrylate. The details of DHPDs intended to be included in this invention are set forth inter alia, in the above-referenced U.S. application Ser. No. 11/068,298, filed on Feb. 27, 2005, above incorporated by reference herein as follows:

Yet more specifically this invention comprises dihydroxyphenyl (DHPD) adhesive compound of formula (I) wherein

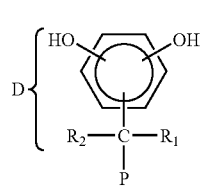

(I)

$R_1$ and $R_2$ may be the same or different and are independently selected from the group consisting of hydrogen, saturated and unsaturated, branched and unbranched, substituted and unsubstituted $C_{1-4}$ hydrocarbon;

P is separately and independently selected from the group consisting of —$NH_2$, —COOH, —OH, —SH,

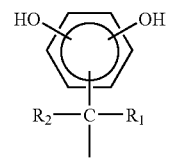

wherein $R_1$ and $R_2$ are defined above.
a single bond, halogen,

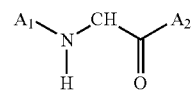

wherein $A_1$ and $A_2$ are separately and independently selected from the group consisting of H, a single bond; a protecting group, substantially poly(alkyleneoxide),

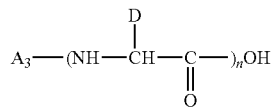

wherein n ranges between 1 and about 3 and $A_3$ is

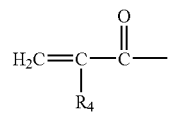

$R_4$ is H, $C_{1-6}$ lower alkyl, or

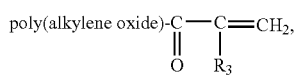

$R_3$ is defined as above, and D is indicated in Formula (I).

In one aspect the poly(alkylene oxide) has the structure

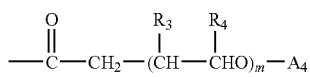

wherein $R_3$ and $R_4$ are separately and independently H, or $CH_3$ and m has a value in the range between 1 and about 250, $A_4$ is —$NH_2$ COOH, —OH, and —SH, —H or a protecting group.

In a very preferred form, DHPD is

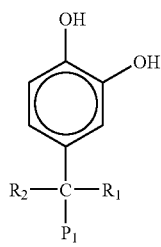

$R_1$, $R_2$, and P being defined as above.

In a further preferred form DHPD is of the structure:

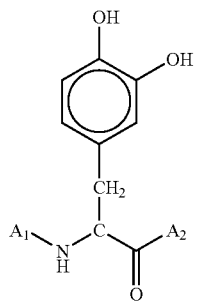

wherein $A_2$ is —OH and $A_1$ is substantially poly(alkylene oxide) of the structure

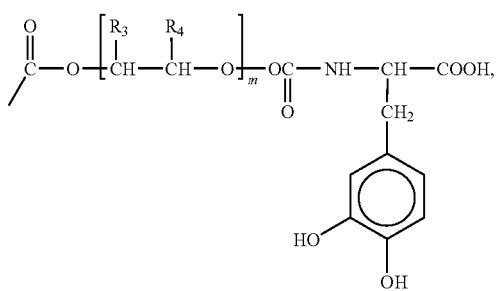

$R_3$, $R_4$ and m being defined above. Generally speaking the poly(alkylene oxide) is a block copolymer of ethylene oxide and propylene oxide.

These dihydroxyphenyl derivative ("DHPD") adhesives function in an aqueous environment. To form the polymeric composition, a DHPD moiety which generally provides adhesive functionality coupled to a polymer which provides the desired surface active effect. These components will be described in more detail below.

Adhesive Moiety

The adhesive moiety of the present invention is a dihydroxyphenyl derivative ("DHPD") having the following preferred structure:

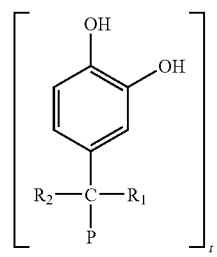

wherein $R_1$, $R_2$, and P are defined above and t ranges between 1 and about 10, preferably about 1 to about 5 and most preferably 1 to about 3. The DHPD adhesive can function in an aqueous environment. In this context, an aqueous environment is any medium comprising water. This includes without limitation water, including salt water and fresh water, cell and bacterial growth media solutions, aqueous buffers, other water-based solutions, and body fluids. The DHPD moiety can be derivatized. As would be understood by those skilled in the art, such derivatization is limited by the retention of the desired adhesive characteristic.

Polymeric Component

Various polymeric components providing a surface active effect and other desired characteristics will be well-known to those skilled in the art made aware of this invention. The desired surface active effect relates to reduced particulate agglomeration and anti-biofouling, including resistance to cell and/or protein adhesion. For instance, the polymer component can be water soluble, depending upon end-use application, and/or capable of micelle formation depending upon various other end-use applications. Polymers useful in the present invention include, but are not limited to, polyethylene glycol (PEG), polyethylene oxide (PEO), polypropylene oxide (PPO), PEO-PPO-PEO block copolymers, polyphenylene oxide, PEG/tetraglyme, PMEMA, polyMPC, and perfluorinated-polyethers.

The polymeric compositions can be synthesized in several ways. For example, the polymeric compositions may be synthesized through a general synthetic procedure for polymer end-group activation. Various polymers or monomeric components thereof can be activated using carbonate chemistry. In particular, a succinimidyl carbonate-activated polymeric component reacted with DHPD moiety can provide a stable urethane conjugate. Two of the many possible pathways (a) and (b) in Scheme 1a and 1b, below, show coupling with a poly(alkylene oxide) in either aqueous or non-aqueous solvents, without compromising desired bio-adhesion. For instance, a DHPD residue can be coupled to a polymeric component to provide the desired conjugate composition, through either urethane or amide bond formation. These synthetic routes are shown in Scheme 1a and 1b which are discussed in greater detail below.

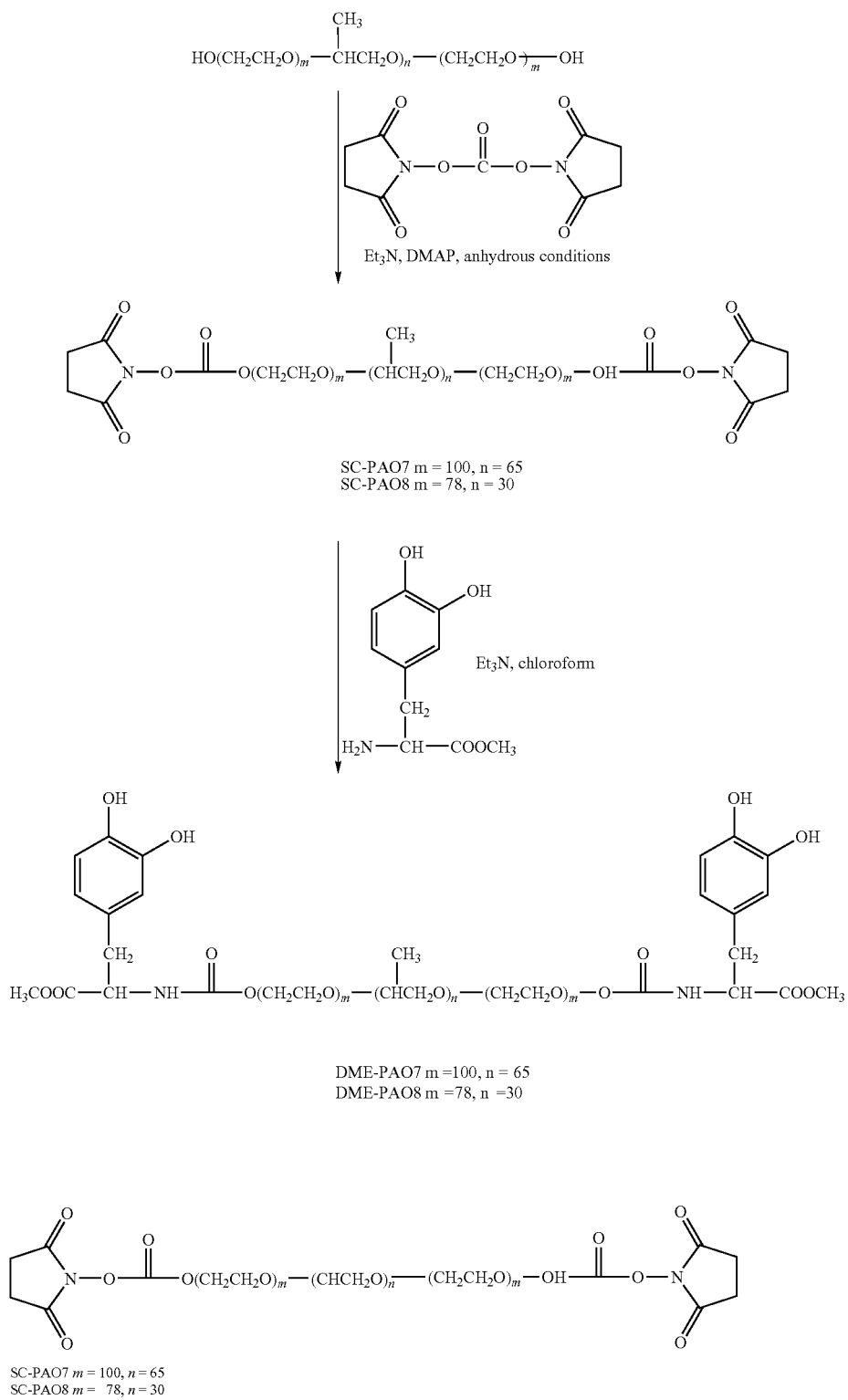

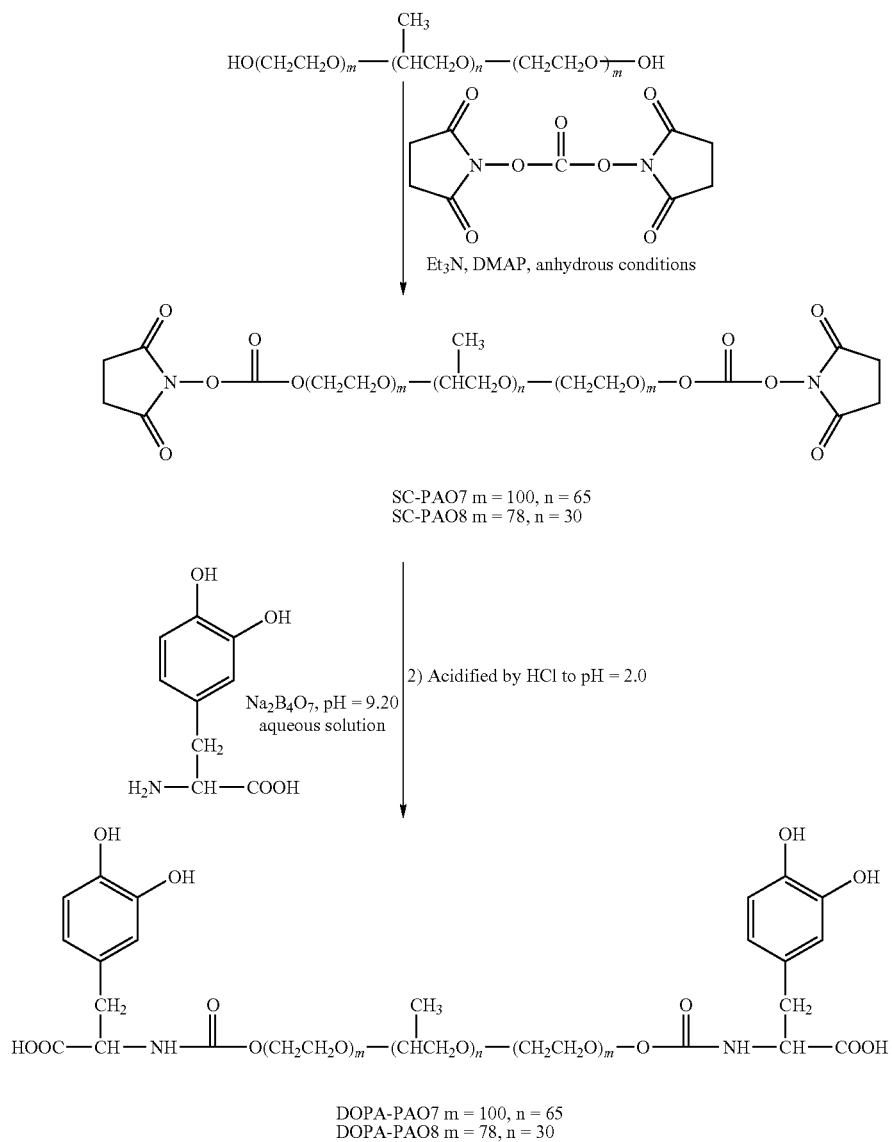

More particularly, if coupled to the polymeric component via urethane bond formation, a carboxylic acid group of the DHPD component can be esterified or derivatized with various other functional groups. Alternatively, the DHPD component can be coupled to a polymeric component (e.g., amidation or esterification depending on polymer end group, —H$_2$ or —OH) providing a DHPD functionality which can be derivatized by any of numerous known protecting groups, including without limitation Boc, Fmoc, borate, phosphate, and tributyldimethylsilyl. N-group protection of a DHPD component can leave the carboxylic acid group available for multi-functional derivatization and/or a higher density of polymeric components conjugated therewith.

Accordingly, in part, the present invention is also a method of using urethane synthesis to incorporate a DHPD residue into a polymeric system. Such a method includes (1) providing a polymeric component terminating in a plurality of monomers, each having a functional end group; (2) preparing a carbonate derivative of the polymeric component; and (3) preparing a urethane moiety upon reaction of the carbonate derivative and at least one DHPD moiety. As described above, a polymeric component utilized in conjunction with this method can include those having terminal monomeric functionality reactive with a reagent providing the desired carbonate derivative and, ultimately, providing a urethane moiety coupling the polymeric and DHPD components. Various other coupling reagents and/or hydroxy-terminating polymeric components can be used to provide the desired urethane moiety.

In part, the present invention is also a method of using a carbonate intermediate to maintain catecholic functionality of a DHPD-incorporated polymeric composition and/or system, or to otherwise enhance the adhesion properties thereof. Such a method includes (1) providing a polymeric component terminating in a plurality of monomers each having a functional end group; (2) reacting the polymeric component with a reagent to provide a carbonate intermediate; and (3) reacting the carbonate intermediate with at least one DHPD moiety. Without limitation to any single theory or mode of operation, this inventive method can be considered a way enhancing the reactivity of the polymeric component end group, via a suitable carbonate intermediate. Subsequent reaction at the amino-nitrogen of DHPD moiety provides the corresponding conjugate while maintaining catecholic functionality.

In accordance with this invention, as demonstrated in Scheme 1a, various synthetic routes can be used to couple DHPD moieties to such carbonate activated intermediates, DOPA methyl ester (DME), prepared by the reaction of DOPA with methanol in the presence of thionyl chloride, can be used in organic solvents. Reaction progress can be monitored by TLC and NMR, with the coupling reaction virtually complete in one hour (with representative conjugates DME-PAO7 (from PAG PLUIRONIC ® F68)). High product yields were obtained upon purification from cold methanol.

The free carboxylic form of DOPA can be coupled with the carbonate intermediate in alkaline aqueous solution. It is well known that the chief difficulty in working with DOPA is its ease of oxidation (to DOPA-quinone and other products), which readily occurs in alkaline aqueous solutions. To prevent unwanted oxidation of DOPA catechol side chains during coupling under alkaline conditions, a borate-protected DOPA can be first formed by adding DOPA to aqueous sodium borate (Scheme 1b). The resulting complex is remarkably stable in neutral or alkaline solutions, and can be readily deprotected under acidic conditions. Taking advantage of complexation between DOPA and borate, DOPA was coupled to the ends of several commercially-available PAOs under alkaline aqueous conditions to yield DOPA-PAO7 and DOPA-PAO8. Visual inspection of the reaction solution revealed the absence of strongly absorbing DOPA-quinone, an indication that DOPA remains unoxidized during the reaction. At the completion of the reaction, acidification with HCl resulted in deprotection of the DOPA endgroups of the block copolymer.

Based on the assumption of two available succinimidyl carbonate groups in the corresponding carbonate intermediates, SC-PAO7 and SC-PAO8, coupling efficiencies of DOPA methyl ester and DOPA to these two PAOs were quantitatively found to be in the range from 76% to 81% as obtained from colorimetric analysis (Table 1). The reported coupling efficiencies are the average values of at least three repeated syntheses performed under the same conditions and were not found to increase significantly when a larger excess of DOPA was used in the reaction. Similar coupling efficiencies were also found for DOPA-PAO7 and DOPA-PAO8 made from aqueous solutions, suggesting that the hydrolysis of succinimidyl carbonate activated PAOs is slow in the aqueous alkaline solution containing $Na_2B_4O_7$.

In contrast to coupling efficiencies, the product yields (shown in Table 1) of the selected DOPA-modified PAOs synthesized in aqueous solution were found to be lower than those synthesized in organic solvent. This may be due to the surfactant properties of the starting PAO material, causing the low efficiency of extraction of DOPA-modified PAO with dichloromethane from water. It should be noted that the free carboxylic acid in DOPA-PAO7 and DOPA-PAO8 can be further functionalized using standard peptide chemistry to tailor the properties of the block copolymers. The four DOPA-modified PAOs of Table 1 could be stored at −20° C. indefinitely with no discoloration or change in properties.

TABLE 1

Coupling efficiency and product yield of DOPA and modified PLURONIC ®

|  | Coupling Efficiency (%)* | Product Yield (%) |
|---|---|---|
| DME-PAO7 | 78.0 ± 4.0 | 75.0 ± 5.0 |
| DOPA-PAO7 | 80.0 ± 4.0 | 52.0 ± 3.0 |
| DME-PAO8 | 76.0 ± 2.0 | 76.0 ± 4.0 |
| DOPA-PAO8 | 81.0 ± 2.0 | 49.0 ± 2.0 |

*Determined by colorimetric analysis as taught by Waite and Benedict (Waite, J. H. & Benedict, C. V. Assay of dihydroxyphenylalanine (DOPA) in invertebrate structural proteins. Methods in Enzymology 107, 397-413 (1984), which is incorporated herein by reference.)

Control of cell and protein adhesion on surfaces is critical to the performance of biosensors, medical diagnostic products, any instrumentation and assays used requiring handling serum and other human/animal fluids, tissue engineering, localized in vivo drug delivery, implanted medical devices, healing of surgical incisions, adhesion of tissues such as bone and cartilage for healing, and nanotechnology (nanoparticle-based therapies and diagnostic tools). In many industrial applications, control of cellular and protein adhesion to surfaces is also important. Such applications include without limitation prevention of mussel attachment to boats and ships, piers, and other structures used in oceans and fresh water, prevention of algal and bacterial growth on water lines used for industrial and drinking water, and sensors used to measure water quality and purity.

The polymeric compositions of the present invention can be used as coatings to prevent protein and cellular adhesion to devices for medical and research applications. These include without limitation such uses as coatings for medical implants, coatings for surgical devices, coatings for devices that handle serum and other animal or human-derived materials, medical diagnostic devices, and biosensors. Alternatively, the polymeric compositions can be tissue adhesive polymeric hydrogels for medical uses such as tissue sealants, gels for prevention of surgical adhesion (scar tissue formation), bone and cartilage adhesives, tissue engineering, and site specific drug elution and for research uses such as immobilization of proteins including antibodies and small molecule analytes including pharmaceuticals. In addition, there are various industrial and consumer product uses of these coatings and hydrogels including without limitation prevention of marine biofouling (attachment of algae, bacteria, and mussels to surfaces underwater), prevention of bacteria contamination of water streams to industrial plants such as electronic and drug manufacturers, prevention of bacterial contamination of drinking water streams, dental and denture adhesives, underwater adhesives to deliver indicators, coatings for water purity and measurement sensors, paints used for prevention of biofouling, and use in cosmetics to adhere desired fragrances and colorants to hair, eyelids, lips, and skin, to form temporarily skin coloring such as tattoos and the like, and for resealable adhesives for consumer products such as storage bags. The present methods can be used to prepare a variety of polymer modified surfaces for both medical (diagnostics, devices, nanoparticle-based therapies) and nonmedical (paints and other particle dispersions, MEMS, quantum dots, nonfouling surfaces) technologies.

Adhesive hydrogels can be also formed using the present methods. The DHPD adhesive is attached to polymers capable of forming hydrogels in vivo or in vitro. These hydrogels can be formed by a number of methods including the use of self-assembling polymers that form gels at higher temperatures such as normal human body temperatures, the use of polymers that can be cross-linked by an enzymatic reaction, the use of polymers that can be subjected to oxidation to form cross-linked hydrogels, and the use of polymers that can be subjected to photoactivation to produce cross-linked hydrogels.

DETAILED DESCRIPTION OF THE INVENTION

The adhesive properties of the preferred anchoring protein moieties of this invention are believed to be due to the presence of a preferred DHPD, namely L-3,4-dihydroxyphenylalanine (DOPA), an amino acid that is formed by post-translational modification of tyrosine. Of the several blue mussel (Mytilus edulis) adhesive pad proteins identified in the art, Mefp-3 and Mefp-5 are of special interest because these proteins have high DOPA content and are structurally located closest to the interface between the adhesive pad and substrate. See, Waite, J. H. and X. Qin, *Polyphosphoprotein from the Adhesive Pads of Mytilus edulis*. Biochemistry, 2001. 40: p. 2887-2893. Papov, V. V., et al., *Hydroxyarginine-containing Polyphenolic Proteins in the Adhesive Plaques of the Marine Mussel Mytilus edulis*. Journal of Biological Chemistry, 1995. 270(34): p. 20183-20192. At approximately 27%, Mefp-5 has the highest DOPA content of any isolated MAP. Furthermore, over 75% of the DOPA residues in Mefp-5 are immediately adjacent to lysine (Lys) residues.

Figure 1:
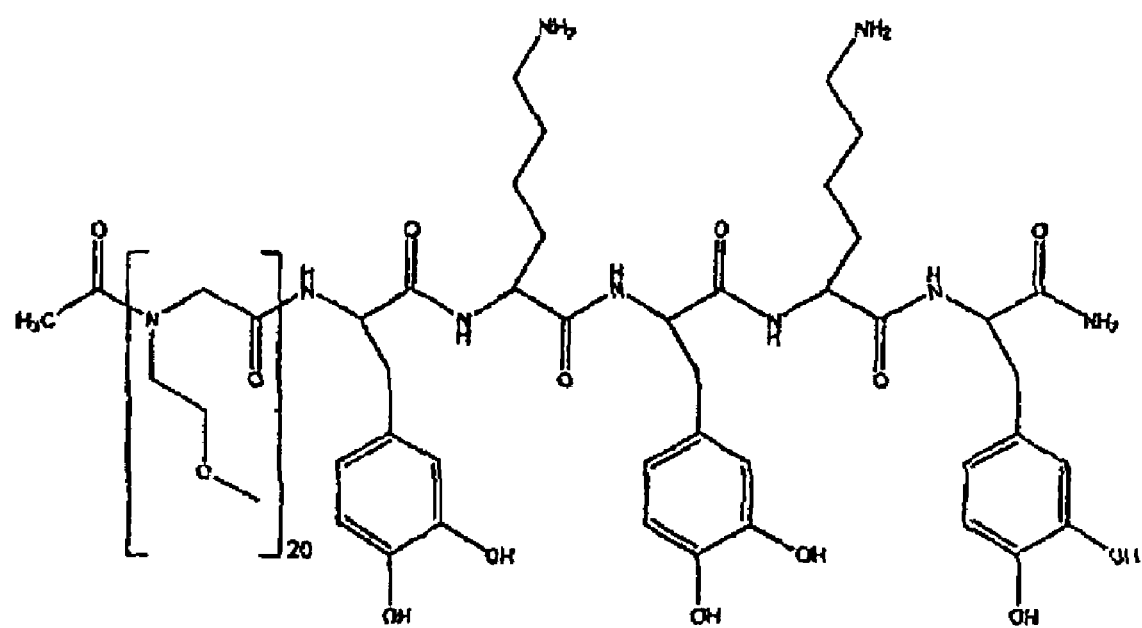
FIG. 1 illustrates the molecular structure of a preferred peptidomimetic polymer composition of this invention.

Accordingly, various non-limiting embodiments can employ a 5-mer peptide mimic of Mefp-5 comprising alternating DOPA and Lys residues (FIG. 1) as an anchor for polymer immobilization. Without restriction to any one theory or mode of operation, the catechol side chains of the DOPA residues are hypothesized to form charge transfer complexes to metal oxide surfaces, whereas the cationic nature of the Lys residues should provide electrostatic attraction to a negatively charged oxide surface. Other DOPA-containing peptide anchor components useful in conjunction with the present inventive polymers will be understood by those skilled in the art made aware of this invention, such components including but not limited to those described in co-pending application Ser. No. 10/199,960 (U.S. Patent Application Publication 2003-0087338 published May 8, 2003 particularly paragraphs [0089] through [0092]) and application Ser. No. 10/699,584 (U.S. Patent Application Publication 2004/026595 published Dec. 30, 2004), filed Jul. 19, 2002 and Oct. 31, 2004, respectively, each of which is specifically incorporated herein by reference in its entirety.

An antifouling portion of the polymer can comprise a poly-N-substituted glycine oligomer (peptoid) of variable length. Peptoids are non-natural mimics of peptides that have a protein-like backbone, with side chain derivatization at the amide nitrogen instead of the alpha-carbon Formula II. A wide range of N-substituents, corresponding N-substituted glycine residues and related peptoid components will be understood by those skilled in the art made aware of this invention, such residues and peptoid components as can be prepared as described below, in the referenced prior art, U.S. Pat. No. 6,887,845, and/or in co-pending application Ser. No. 11/120,071 filed May 2, 2005, each of which is incorporated hereby by reference.

In certain embodiments, the peptoid component can comprise an N-substituted methoxyethyl side chain, according to current understanding in the art of functional groups that provide fouling resistance to surfaces. In an extensive study of protein adsorption onto functionalized SAMs, certain functional group characteristics were identified that render surfaces resistant to protein adsorption. They include hydrophilicity, hydrogen-bond acceptors but not hydrogen-bond donors, and electrical charge neutrality. See, Ostuni, E., et al., *A Survey of Structure-Property Relationships of Surfaces that Resist the Adsorption of Protein*. Langmuir, 2001. 17: p. 5605-5620 which is incorporated by reference herein. Like PEG and PMEA components, the methoxyethyl side chain of such polypeptide exhibits all four of these characteristics, including hydrophilicity, hydrogen bond acceptors, no hydrogen bond donors, and no charge. N-substituent identity is limited only by functional effect, meeting one or more of the aforementioned characteristics and/or otherwise demonstrating antifouling properties upon incorporation or one or more such moletics into a corresponding peptoid polymer component. With respect to the chemical properties of the peptoid backbone, side chain substitution from the nitrogen (instead of the alpha carbon peptides) eliminates the amide hydrogen, removes the capacity for hydrogen bond donation, and significantly decreases incidence of protease degradation.

Figure 2:
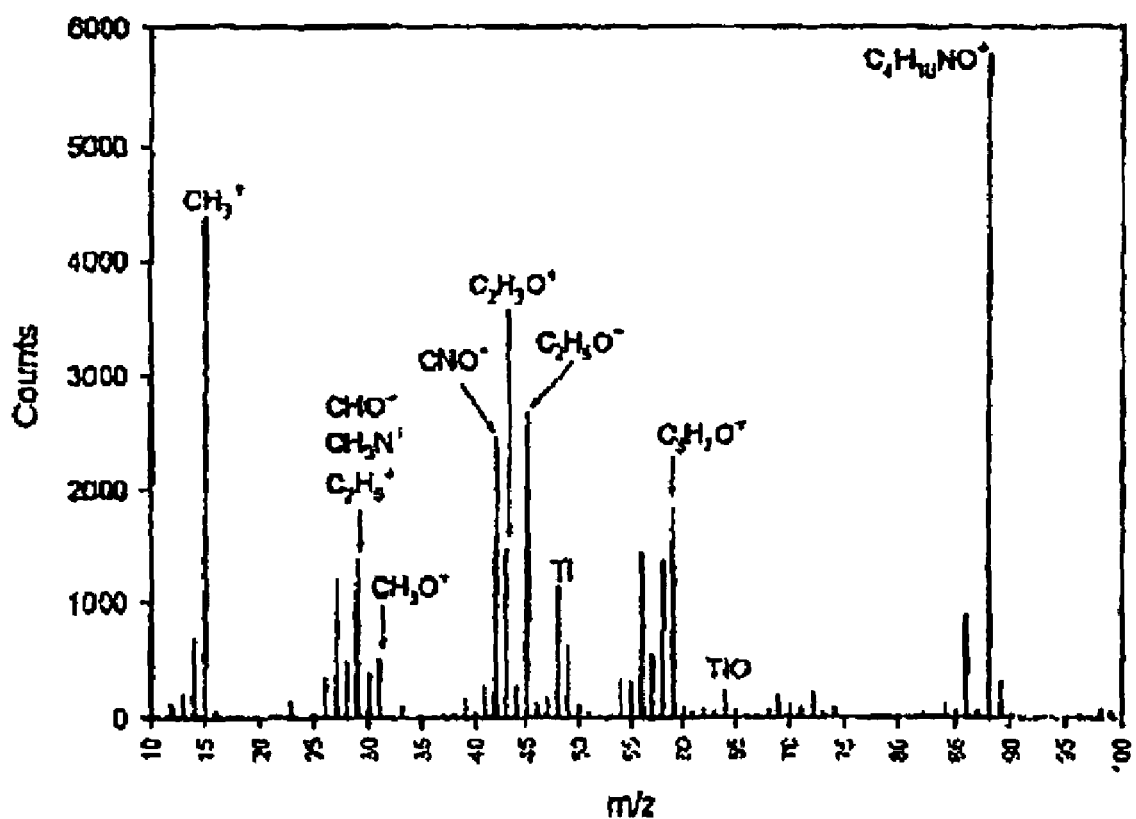
FIG. 2 shows the low mass region of the positive ion ToF-SIMS spectra of Ti modified with a peptidomimetic polymer coating.
Figure 3:
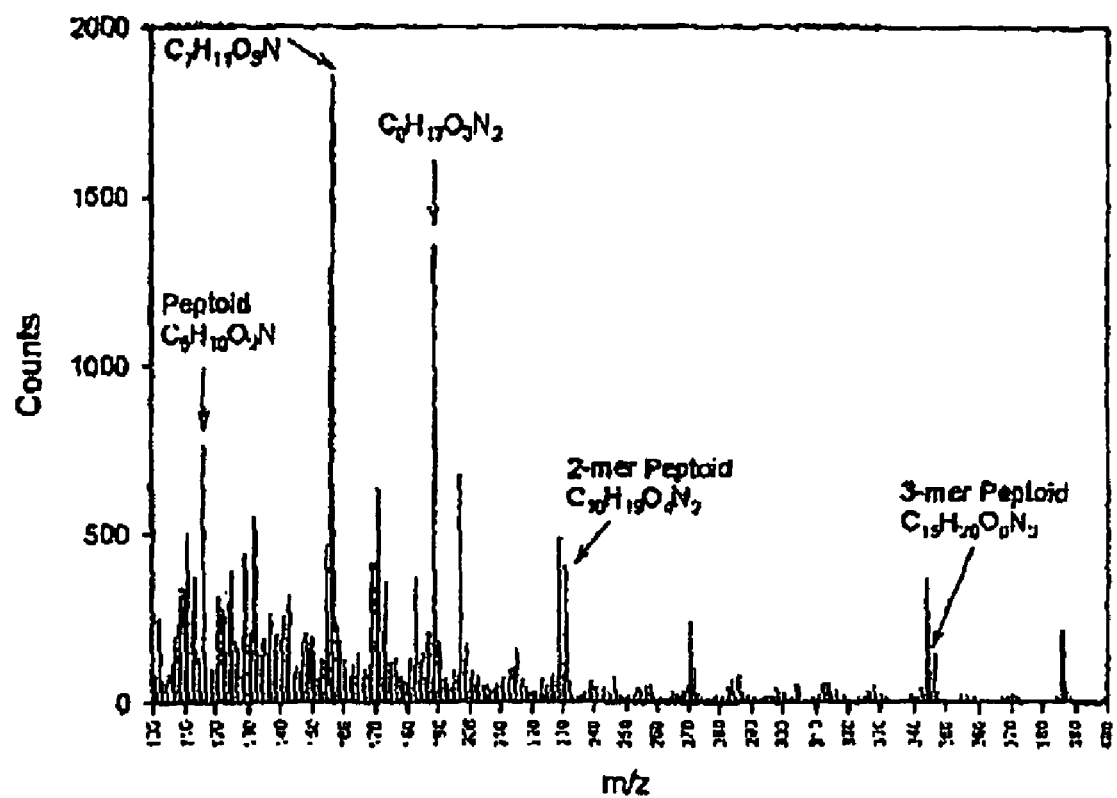
FIG. 3 shows mid-range mass region of the negative ion ToF-SIMS spectra of Ti modified with peptidomimetic polymer.

The chimeric peptide-peptoid molecule shown in Scheme 1 was synthesized on solid phase resin by first synthesizing the adhesive peptide anchor with standard Fmoc strategy followed by synthesis of a 20-mer N-methoxyethyl glycine peptoid using a known submonomer protocol. See, Zuckerman, R. N., et al., *Efficient Method For the Preparation of Peptoids [Oligo(n-Substituted Blycines)] By Submonomer Solid-Phase Synthesis*. Journal of the American Chemical Society, 1992. 114(26): p. 10646-10647. The amine terminus was acetylated, cleaved from the resin, purified by RP-HPLC and analyzed by mass spectrometry. Silicon wafers coated with 20 nm of electron beam evaporated Ti were modified by adsorption of the peptidomimetic polymer from an aqueous solution. Unmodified and modified Ti surfaces were analyzed by time-of-flight secondary ion mass spectrometry (ToF-SIMS) and X-ray photoelectron spectroscopy (XPS). The positive ion ToF-SIMS spectrum of unmodified Ti (not shown) exhibited typical low intensity hydrocarbon contamination peaks $(C_nH_{2n-1}^+)$ and $(C_nH_{2n-1}^+)$, a Ti peak at m/z=47.95 and a $TiO^1$ peak at m/z=63.95. The positive ion ToF-SIMS spectrum of peptoid modified Ti revealed numerous fragments representing the presence of adsorbed peptoid polymer (FIG. 2). Apparent fragmentation of the methoxyethyl side chain gave rise to peaks for $CH_3^1$ (m/z=15) $C_2H_5O^+$ (m/z=45.06) and $C_3H_7O^+$ (m/z=59.07) fragments, as well as Lys-derived fragments such as $C_2NH_4^+$ (m/z=42.0). The negative ion spectrum contained peaks for 1-, 2- and 3-mer peptoid fragments as well as other large fragments of the peptoid portion of the polymer (FIG. 3).

Figure 4:
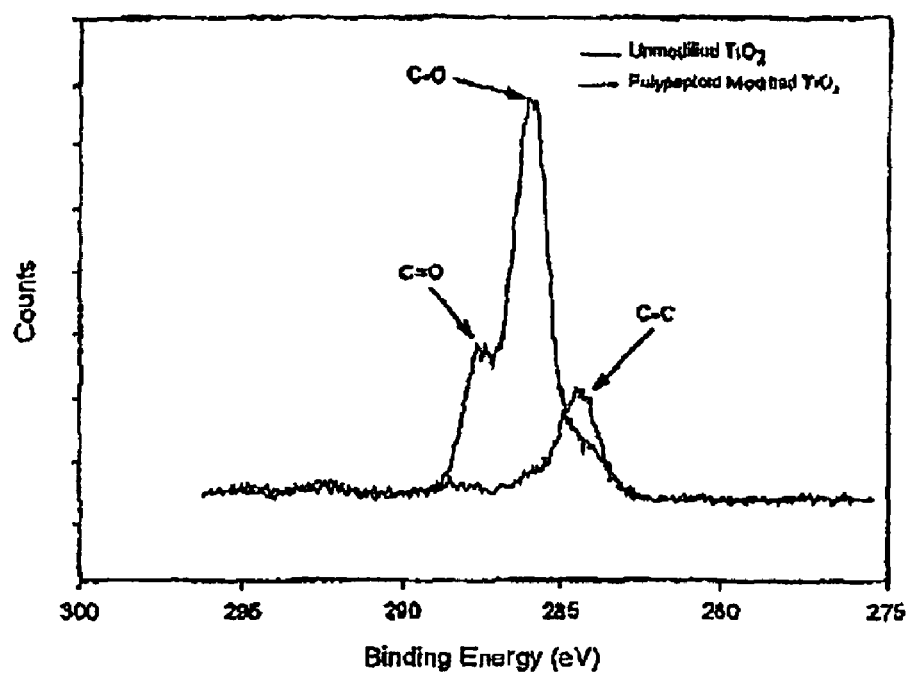
FIG. 4 is a high resolution C(1s) XPS spectra of unmodified and polypeptoid modified $TiO_2$ substrates.
Figure 5:
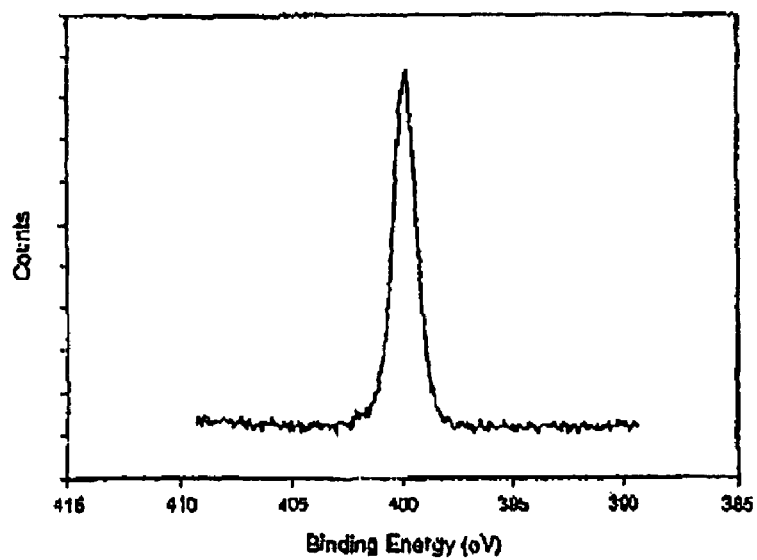
FIG. 5 is a high-resolution N(1s) XPS spectra of polypeptoid modified $TiO_2$ substrate.

XPS analysis of the surfaces modified with the peptidomimetic polymer reveals further evidence of peptidomimetic polymer adsorption onto the Ti surface. XPS spectra showed an increase in the ether (C—O) peak at 286.0 eV when compared to control Ti surfaces (FIG. 4). A peak at 284.6 eV is due to the aliphatic and aromatic carbons in the methoxyethyl side chain and the DOPA anchoring group, as well as hydrocarbon contamination. The carbonyl groups of the peptidometic polymer backbone are represented by a peak at 287.5 eV. Furthermore, a strong N(1s) peak was present at 399.7 eV in the spectra of the polypeptoid modified surfaces that was not observed in the unmodified Ti surfaces (FIG. 5). While certain embodiments of this invention are demonstrated in conjunction with a titanium oxide substrate, it will be understood by those skilled in the art that various other materials, including but not limited to other metal oxides, can be employed with composites and/or compositions comprising any one or a plurality of the peptidomimetic polymers of this invention. Other such materials include those recognized in the art for implementation of the medical and non-medical applications mentioned herein.

Figure 6:
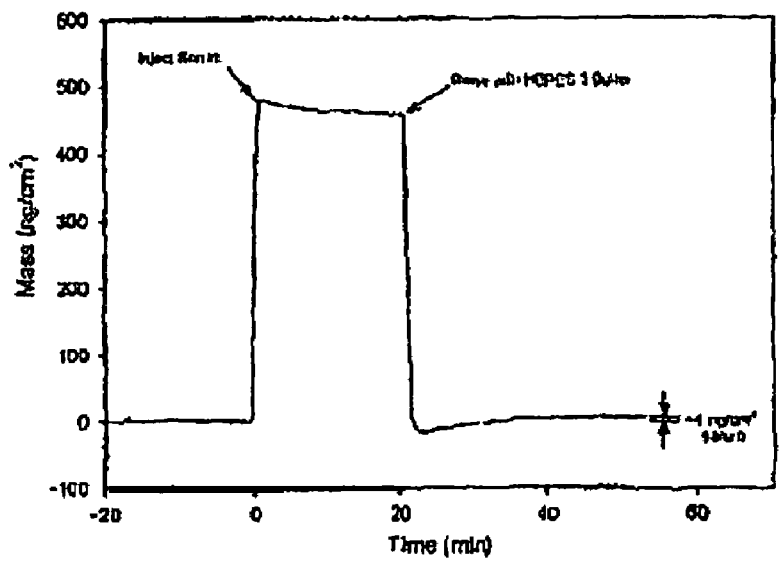
FIG. 6 is a mass plot of scrum protein adsorption on peptoid modified Ti waveguide as measured by OWLS.

Optical waveguide lightmode spectroscopy (OWLS) experiments revealed that polypeptoid modification of titanium surfaces resulted in a substantial reduction in protein adsorption (FIG. 6). Exposure of unmodified Ti waveguides to whole human serum for 20 minutes resulted in an adsorbed protein layer with a mass between 150 and 230 ng/cm$^2$ after rinsing. However, surprisingly and unexpectedly, serum protein adsorption onto representative peptoid modified substrates of this invention under identical conditions was reduced to approximately 4 ng/cm$^2$. This amount of protein adsorption is similar to that adsorbed onto DOPA-anchored PEG coatings and to oligoethylene glycol terminated SAMs, demonstrating the excellent protein resistance of peptidomimetic polymer compositions of the invention.

Figure 7:
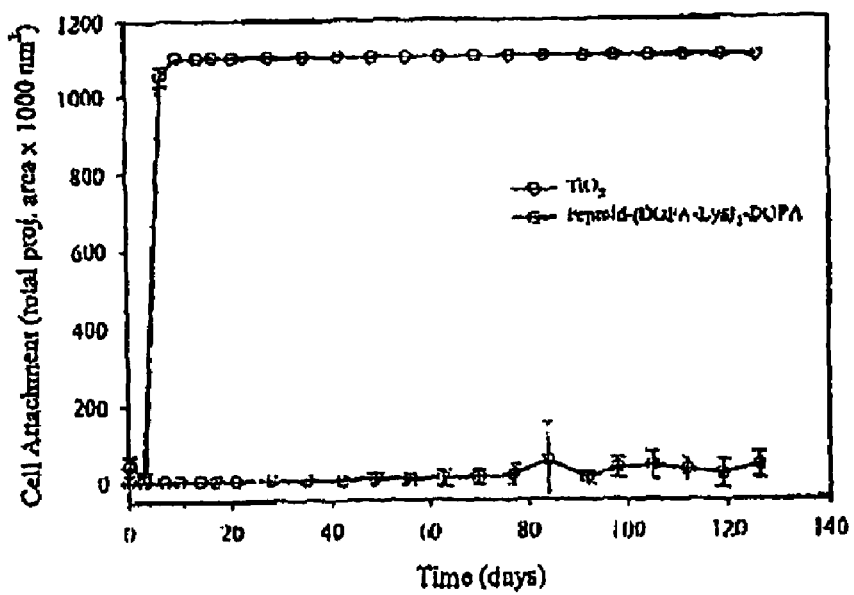
FIG. 7 is a total projected cell area of 3'1'3 fibroblasts on $TiO_2$ and peptoid modified $TiO_2$. Cells were reseeded twice weekly throughout the duration of the experiment.

Finally, the ability of polypeptoid modified surfaces to resist cell attachment over a long period of time was determined by culturing 3T3 fibroblast cells on unmodified and modified titanium surfaces in the presence of serum. Fresh cells were seeded twice weekly onto the titanium surfaces for several months, the cell attachment at various time points assayed by fluorescence microscopy and image analysis. Although fibroblasts readily attached to unmodified titanium surfaces and were nearly confluent after several days (FIG. 7), the peptoid modified surfaces exhibited low levels of cell attachment throughout the experiment. Since cell attachment to surfaces is typically mediated by adsorbed protein, the results infer that serum protein adsorption remained low throughout the course of the in vitro experiment.

It is interesting to note that fouling resistance persisted for many days in the presence of serum, which typically contains protease enzymes that would be expected gradually to degrade peptide bonds of the polymer backbone. In this respect as well, the design of the peptoid is beneficial in that the placement of the side chain on the amide nitrogen leads to an essentially protease-resistant backbone. Although the adhesive peptide anchor of the molecule may be susceptible to protease degradation, at high polymer density on the surface the peptide anchors are likely to be buried beneath or protected by the peptoid chains and therefore essentially inaccessible to serum proteases.

As illustrated, above, a new de novo designed peptidomimetic polymers of this invention were synthesized and determined to have excellent and long-lasting antifouling properties when immobilized onto a metal oxide surface. Such chimeric compounds can comprise a mussel adhesive protein mimetic peptide for robust water-resistant anchorage onto substrates, coupled to an oligometric N-substituted glycine peptoid with a side chain (e.g., methoxyethyl) designed for resistance to protein and cell fouling. The modular, solid phase approach known in the art used to synthesize these peptidomimetic polymers offers precise control of molecular weight at high yields, and with virtually unlimited versatility in functionality obtained through variation of N-substituted side chain composition in the form of both natural and non-natural side chains. See, Zuckerman, R. N., et al., *Efficient Method For the Preparation of Peptoids [Oligo(N-Substituted Glycines)] By Submonomer Solid-Phase Synthesis*. Journal of the American Chemical Society, 1992. 114(26): p. 10646-10647. Kirshenbaum, K., et al., Sequence-specific polypeptoids: *A diverse family of heteropolymers with stable secondary structure*. PNAS, 1998. 95(8): p. 4303-4308. The synthetic diversity available through such peptidomimetic polymers can be used to better understand the fundamental relationship between chemical composition of polymers and protein/cell resistance. Enhanced understanding of these relationships may, in turn, lead to improved antifouling strategies for medical and nonmedical applications.

EXAMPLES

Materials

Bromoacetic acid (BAA) and methoxyethylamine were purchased from Aldrich (Milwaukee, Wis.).

Polymer Synthesis

A peptidomimetic polymer composition of the invention was synthesized on 0.25 mmol Fmoc-Rink amide resin (Nova Biochem, San Diego, Calif.) using an ABI 433A (Applied Biosystems, Foster City, Calif.) automated peptide synthesizer. Conventional Fmoc strategy of solid phase peptide synthesis with Fmoc-Lys-(N-Boc) and Fmoc-DOPA (acetonid) amino acids (Nova Biochem, San Diego, Calif.) was used to synthesize the C-terminal DOPA-Lys-DOPA-Lys-DOPA peptide anchor, after which the polypeptoid portion was synthesized using submonomer protocol described previously. See Zuckerman, supra. Bromoacetylation of the N-terminal amino was accomplished by vortexing 4.15 mL of 1.2M bromoacetic acid in DMF and 1 mL of diisopropylcarbodiimide (DIC) (Aldrich, Milwaukee, Wis.) with the resin for 60 min. After rinsing 4 times with 7 mL of DMF, the resin was vortexed for 60 min. with 4 mL of 1M methoxyethylamine (Aldrich, Milwaukee, Wis.) in N-methylpyrrolidone (NMP) (Applied Biosystems, Foster City, Calif.) to introduce the side chain moiety. The liquid was then drained and the resin washed with 7 mL of DMF. These two reaction cycles were repeated until the desired number of peptoid monomers was obtained.

Following completion of the synthesis, the N-terminus of the peptidomimetic polymer was acetylated with acetic anhydride (Applied Biosystems, Foster City, Calif.). Cleavage of the peptidomimetic polymer from the resin deprotection of the amino acid side chains was accomplished by treating the resin with 95% (v/v) trifluoroacetic acid (Acres Organics, Belgium) with 2.5% H$_2$O and 2.5% triisopropylsilane (Aldrich, Milwaukee, Wis.). The cleaved peptidomimetic polymer was isolated by filtration and rinsed several times with acetonitrile and water. The crude product was analyzed by reversed-phase HPLC using a Vydac C18 column and ESI-MS for purity and composition. Purification was performed by preparative HPLC, and purified fractions were frozen at −85° C. and lyophilized.

Substrate Preparation

Silicon wafers were coated with 20 nm of electron beam evaporated Ti and then cut into 8 mm by 8 mm pieces. The substrates were cleaned ultrasonically for ten minutes in 2-propanol, dried under $N_2$ and then exposed to $O_2$ plasma (Harrick Scientific Ossining, USA) at $\leq$50 Torr and 100 W for three minutes to produce a clean titanium oxide surface. OWLS waveguides were purchased from Microvacuum Ltd. (Budapest, Hungary), consisting of a $SiO_2$ substrate coated with $Si_{6.25}Ti_{6.75}O_2$ and a final 10 nm thick coating of $TiO_2$ produced by a sol-gel process. Voros, J., et al., *Optical grating coupler biosensors*. Biomaterials, 2002. 23: p. 3699-3710. Sensors were cleaned following the same procedure as Ti substrates.

Substrate Modification

Clean substrates and sensors were immersed in 1 mg/ml peptidomimetic polymer in saturated NaCl buffered with 0.1M N-morpholinopropanesulfonic acid (MOPS) at 60° C. for 24 hours to form a uniform monolayer. After modification, substrates were exhaustively rinsed with ultrapure $H_2O$ and dried in a stream of filtered $N_2$.

Surface Characterization

Survey and high resolution XPS spectra were collected on an Omicron FSCALAB (Omicron, Taunusstein, Germany) configured with a monochromated Al K$\alpha$ (1486.8 eV) 300-W X-ray source, 1.5 nm circular spot size, a flood gun counter charging effects, and an ultrahigh vacuum ($<10^{-8}$ Torr). The takeoff angle, defined as the angle between the substrate normal and the detector, was fixed at 45°. Substrates were mounted on standard sample studs by means for double-sided adhesive tape. All binding energies were calibrated using the C(1s) carbon peak (284.6 eV). Analysis included a broad survey scan (50.0 eV pass energy) and a 10-min. high-resolution scan (22.0 eV pass energy) at 270-300 eV for C(1s) and, comparably, for N(1s).

Secondary ion spectra were recorded on a TRIFT III time-of-flight secondary ion mass spectrometer (Physical Electronics, Eden Prairie, Minn) in the mass range 0-2000 m/z. A Ga-source was used at a beam energy of 15 keV with a 100 μm raster size. Positive and negative spectra were collected and calibrated with a set of low mass ions using the PHI software Cadence.

Cell Culture

3T3-Swiss albino fibroblasts (ATCC, Manassas, Va.) were maintained at 37° C. and 5% $CO_2$ in Dulbecco's modified Eagle's medium (DMEM, Cellgro, Herndon, Va.) containing 10% fetal bovine serum (FBS) and 100 μm/ml of penicillin and 100 U/ml of streptomycin. Immediately before use, fibroblasts of passage 12-16 were harvested using 0.25% trypsin-EDTA, resuspended in DMEM with 10% FBS and counted using a hemacytometer.

Quantification of Cell Adhesion

Modified and unmodified $TiO_2$ substrates were pretreated in a 12-well TCPS plate with 1.0 ml of DMEM containing FBS for 30 minutes at 37° C. and 5% $CO_2$. Fibroblasts were seeded onto the test substrates at a density of $2.9 \times 10^3$ cell/$cm^2$. For short-term studies, the substrates were maintained in DMEM with 10% FBS at 37° C. and 5% $CO_2$ for 4 hours, after which adherent cells were fixed in 3.7% paraformaldehyde for 5 minutes and stained with 5 M 1,1'-dioctadecyl-3,3,3',3' tetramethylindocarbocyanine perchlorate (Dil; Molecular Probes, Eugene, Oreg.) for inflorescent microscope counting. For long-term adhesion experiments substrates were reseeded with 3T3 fibroblasts at a density of $2.9 \times 10^3$ cells/$cm^2$ twice per week. The medium was aspirated from each well to remove any non-adherent cells and PBS was used to rinse the substrates and wells. Fibroblasts were stained with 2.5 μM calcein-AM (Molecular Probes) in complete PBS for 1 hour at 37° C. twice per week initially and then once per week after 2 weeks.

Quantitative cell attachment data was obtained by acquiring nine images from random locations on each substrate using an Olympus BX-40 ($\lambda_{Ex}$=549 nm, $\lambda_{Em}$=565 nm) and a Coolsnap CCD camera (Roper Scientific, Trenton, N.J.). The experiments were performed in triplicate for statistical purposes, resulting in a total of 27 images per time point for each substrate. The resulting images were quantified using thresholding in Metamorph (Universal Imaging, Downington, Pa.).

Protein Adsorption

For in situ protein adsorption experiments, $TiO_2$ coated waveguides were modified ex situ with polypeptoid. The waveguides were inserted in the OWLS flow-through cell and equilibrated by exposing to HEPES-2 buffer (10 mM HEPES, 150 mM NaCl, pH 7.4) for at least 6 hours to allow for complete exchange for ions at the $TiO_2$ surface. The measurement head was mounted in the sample chamber and heated to 37° C.; the signal was recorded to ensure a stable baseline and thus adequate equilibrium time. Whole human serum (Control Serum N, Roche Diagnostics, Switzerland, reconstituted in ultrapure water) was injected into the flow-through cell. The waveguide was exposed to serum for 40 minutes and subsequently rinsed with HEPES-2 buffer for another.

The refractive index of solutions was measured in a refractometer (J157 Automatic Refractometer, Rudolph Research (under identical experimental conditions. A refractive index value of 1.33119 was used for the HEPES-2 buffer and a standard value of 0.182 $cm^3$/g was used for the protein-adsorption calculations. The residual increase in signal intensity versus baseline measured by OWLS can be directly correlated to adsorbed mass of protein.

One skilled in this art will be prompted to think of many applications for its present invention in light of this disclosure. The compounds, compositions coatings, and/or composites of this invention can be applied, without limitation, to:

1) Medical Diagnostics and Therapies, including but not limited to
  (a) Preparation of Nonfouling Surfaces for
    Biosensors
    Cardiovascular implants
    Catheters
    Lubricious coatings on catheters, needles, and other percutaneous devices
    Medical tubing (dialysis)
    Implantable electronic devices (MEMS)
    Corrosion resistant coatings on medical grade metal alloys (surface adsorbed catechols are unknown to enhance corrosion resistance of metals); and
  (b) Stabilization of Particles of Diagnostics ad Therapy, such as
    Stabilization of proteins, peptides and other therapeutics under in-vivo conditions
    Nanoparticle-based ex-vivo diagnostics (gold or quantum dot based technologies)
    Nanoparticle-based in-vivo diagnostics
      Paramagnetic nanoparticle contrast agents for MRI
      Nanoparticles for optical imaging
    Nanoparticle-Based Therapies
      Superparamagnetic magnetite nanoparticles for hyperthermia, and 2) Nonmedical Applications, including but not limited to
Corrosion resistant coatings (surface adsorbed catechols and polyphenols are known to enhance corrosion resistance of metals, and polyphenol polymers are currently used as corrosion resistant coatings)
Antifouling coatings on consumer goods (sunglasses, etc.)
Antifouling coatings on electronic devices (MEMS, etc.)
Antifouling/anti-icing coatings on aircraft
Stabilization of quantum dot suspensions
Stabilization of magnetorhcological fluids (ferrofluids)
Stabilization of inorganic particles (TiO2, etc.) in paints Many other such applications will occur to one skilled in the art, in view of the present disclosure.

What is claimed is as follows:

1. A peptidomimetic polymer comprising a polypeptide and a polypeptoid, the polypeptide having the structure:

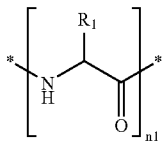

the polypeptoid having the structure:

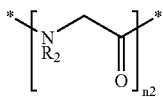

wherein $R_1$ comprises at least one dihydroxyphenyl alone or in combination with an amine-terminated lower alkyl chain having from 1 to about 10 carbon atoms;
wherein $R_2$ comprises at least one ether linkage, wherein each alkyl group or chain of the ether has from 1 to about 10 carbon atoms; $n_1$ has a value in the range of about 1 to about 10; and $n_2$ has a value in the range of about 5 to about 100.

2. A peptidomimetic polymer according to claim 1 wherein $R_1$ comprises

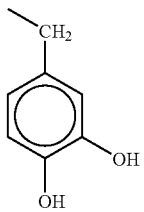

3. A peptidomimetic polymer according to claim 1 wherein
$R_2$ is $-CH_2-CH_2-O-CH_3$.

4. A peptidomimetic polymer according to claim 1 wherein $n_1$ is 3.

5. A peptidomimetic polymer according to claim 1 wherein $n_2$ is 20.

6. A coating comprising a peptidomimetic polymer comprising a polypeptide and a polypeptoid, the polypeptide having the structure:

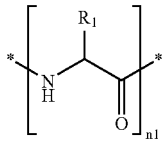

the polypeptoid having this structure:

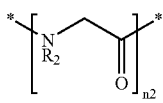

wherein $R_1$ comprises at least one dihydroxyphenyl alone or in combination with an amine-terminated lower alkyl chain having from 1 to about 10 carbon atoms;
wherein $R_2$ comprises at least one ether linkage, wherein each alkyl group or chain of the ether has from 1 to about 10 carbon atoms;
$n_1$ has a value in the range of about 1 to about 10; and
$n_2$ has a value in the range of about 5 to about 100.

7. A coated metal work piece comprising a metal substrate having adhered thereto the peptidomimetic polymer coating of claim 6.

8. A work piece according to claim 7 wherein the metal substrate is a working surface of a medical device.

9. A work piece according to claim 7 wherein the metal substrate comprises titanium oxide.

10. An antifouling resistant coating comprising a polypeptidomimetic polymer comprising an anchoring polypeptide and an antifouling polypeptoid, the anchoring polypeptide having the structure:

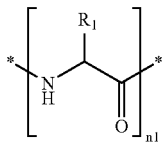

the antifouling polypeptoid having the structure:

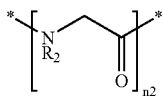

wherein $R_1$ comprises at least one dihydroxyphenyl alone or in combination with an amine-terminated lower alkyl chain having from 1 to about 10 carbon atoms;
wherein $R_2$ comprises at least one ether linkage, wherein each alkyl group or chain of the ether has from 1 to about 10 carbon atoms;
$n_1$ ranges from about 1 to about 10; and
$n_2$ ranges from about 5 to about 100.

* * * * *

UNITED STATES PATENT AND TRADEMARK OFFICE
CERTIFICATE OF CORRECTION

PATENT NO. : 7,618,937 B2
APPLICATION NO. : 11/280107
DATED : November 17, 2009
INVENTOR(S) : Messersmith et al.

Page 1 of 1

It is certified that error appears in the above-identified patent and that said Letters Patent is hereby corrected as shown below:

Column 11, line 62 "dichioromethane" should be -- dichloromethane --

Column 19, claim 1 " 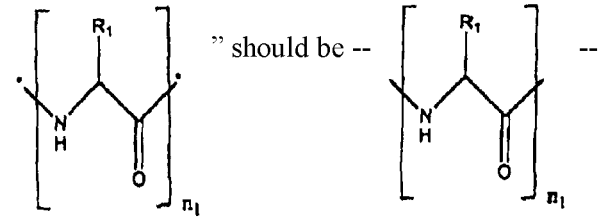 " should be --

Column 19, claim 1 " 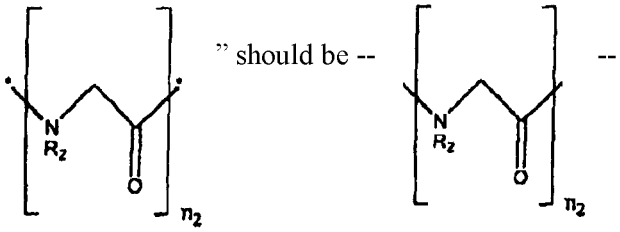 " should be --

Signed and Sealed this

Twenty-third Day of March, 2010

David J. Kappos
*Director of the United States Patent and Trademark Office*